US011763930B2

(12) United States Patent
Abe

(10) Patent No.: US 11,763,930 B2
(45) Date of Patent: Sep. 19, 2023

(54) INFORMATION PROCESSING APPARATUS, RADIOGRAPHING APPARATUS, RADIOGRAPHING SYSTEM, INFORMATION PROCESSING METHOD, AND STORAGE MEDIUM

(71) Applicant: CANON KABUSHIKI KAISHA, Tokyo (JP)

(72) Inventor: Masahiro Abe, Yamato (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 531 days.

(21) Appl. No.: 16/366,038

(22) Filed: Mar. 27, 2019

(65) Prior Publication Data

US 2019/0311794 A1   Oct. 10, 2019

(30) Foreign Application Priority Data

Apr. 4, 2018 (JP) ................................ 2018-072651

(51) Int. Cl.
*G16H 30/40* (2018.01)
*G06T 11/00* (2006.01)
(Continued)

(52) U.S. Cl.
CPC ......... *G16H 30/40* (2018.01); *G06F 3/04845* (2013.01); *G06T 7/0012* (2013.01);
(Continued)

(58) Field of Classification Search
CPC ........ G16H 30/00; G16H 30/20; G16H 30/40; G06F 3/0482; G06F 3/0481;
(Continued)

(56) References Cited

U.S. PATENT DOCUMENTS 8,370,293 B2 * 2/2013 Iwase ..................... G06F 16/22
   707/608
9,002,089 B2 * 4/2015 Grass ....................... G06T 7/32
   382/131
(Continued)

FOREIGN PATENT DOCUMENTS

| CN | 107260190 A | 10/2017 |
| JP | 2003284709 A | 10/2003 |
| JP | 2007244860 A | 9/2007 |

OTHER PUBLICATIONS

Schulz-Menger, J., Bluemke, D.A., Bremerich, J. et al. Standardized image interpretation and post processing in cardiovascular magnetic resonance: Society for Cardiovascular Magnetic Resonance (SCMR) Board of Trustees Task Force on Standardized Post Processing. J Cardiovasc Magn Reson 15, 35 (2013). (Year: 2013).*

(Continued)

*Primary Examiner* — Andrae S Allison
(74) *Attorney, Agent, or Firm* — Carter, DeLuca & Farrell LLP

(57) ABSTRACT

An information processing apparatus includes a purpose setting unit configured to set an examination purpose of radiography, a selection setting unit configured to select processing of a radiation image corresponding to the examination purpose and set the processing in an editing area of a display unit, and a generation unit configured to generate a processing procedure corresponding to the examination purpose based on the set processing.

12 Claims, 16 Drawing Sheets

(51) Int. Cl.
*G16H 40/63* (2018.01)
*G06T 7/00* (2017.01)
*G06F 3/04845* (2022.01)
*G06T 11/60* (2006.01)
*G06F 3/0482* (2013.01)

(52) U.S. Cl.
CPC .......... *G06T 11/005* (2013.01); *G06T 11/008* (2013.01); *G06T 11/60* (2013.01); *G16H 40/63* (2018.01); *G06F 3/0482* (2013.01); *G06T 2207/10116* (2013.01); *G06T 2207/30061* (2013.01)

(58) Field of Classification Search
CPC . G06F 3/04845; G06T 7/0012; G06T 7/0014; G06T 7/0016; G06T 11/005; G06T 11/008; G06T 11/60; G06T 11/80; G06T 2207/10116; G06T 2207/30101; G06T 2207/30104
USPC ................................. 382/131–132, 128, 100
See application file for complete search history.

(56) References Cited

U.S. PATENT DOCUMENTS

| | | | | |
|---|---|---|---|---|
| 10,140,888 | B2* | 11/2018 | Campanatti, Jr. | G06F 19/321 |
| 10,733,730 | B2* | 8/2020 | Mansi | G06T 7/11 |
| 11,335,455 | B2* | 5/2022 | Lee | G06F 18/217 |
| 2014/0379718 | A1* | 12/2014 | Halter | G06F 16/35 707/738 |
| 2016/0213347 | A1* | 7/2016 | Kawanishi | A61B 6/465 |
| 2016/0350919 | A1* | 12/2016 | Steigauf | G16H 40/20 |
| 2018/0101645 | A1* | 4/2018 | Sorenson | G06N 20/00 |
| 2018/0204325 | A1* | 7/2018 | Steigauf | G06F 18/2148 |
| 2018/0263585 | A1* | 9/2018 | Weiss | A61B 6/50 |
| 2019/0279363 | A1* | 9/2019 | Steigauf | G06V 10/451 |
| 2019/0287247 | A1* | 9/2019 | Duchesne | G06T 7/174 |
| 2019/0311794 | A1* | 10/2019 | Abe | G06T 11/005 |
| 2020/0373003 | A1* | 11/2020 | Lyman | A61B 5/7275 |

OTHER PUBLICATIONS

J. Alex Mathew, A. M. Khan and U. C. Niranjan, "Diagnosis of the Abnormality Extracted MRI Slice Images of a GUI Based Intelligent Diagnostic Imaging System," 2011 International Conference on Process Automation, Control and Computing, 2011, pp. 1-6, doi: 10.1109/PACC.2011.5979011. (Year: 2011).*

O'neill, Thomas J., et al. "Active reprioritization of the reading worklist using artificial intelligence has a beneficial effect on the turnaround time for interpretation of head CT with intracranial hemorrhage." Radiology: Artificial Intelligence 3.2 (2020): e200024. (Year: 2020).*

Gaskin, Cree M., et al. "Impact of a reading priority scoring system on the prioritization of examination interpretations." American Journal of Roentgenology 206.5 (2016): 1031-1039. (Year: 2016).*

Arbabshirani, Mohammad R., et al. "Advanced machine learning in action: identification of intracranial hemorrhage on computed tomography scans of the head with clinical workflow integration." NPJ digital medicine 1.1 (2018): (Year: 2018).*

Notice of Reasons for Refusal issued by the Japan Patent Office dated Apr. 11, 2022 in corresponding JP Patent Application No. 2018-072651, with English translation.

First Office Action issued by the China National Intellectual Property Administration dated Nov. 18, 2022 in corresponding CN Patent Application No. 201910255844.3, with English translation.

* cited by examiner

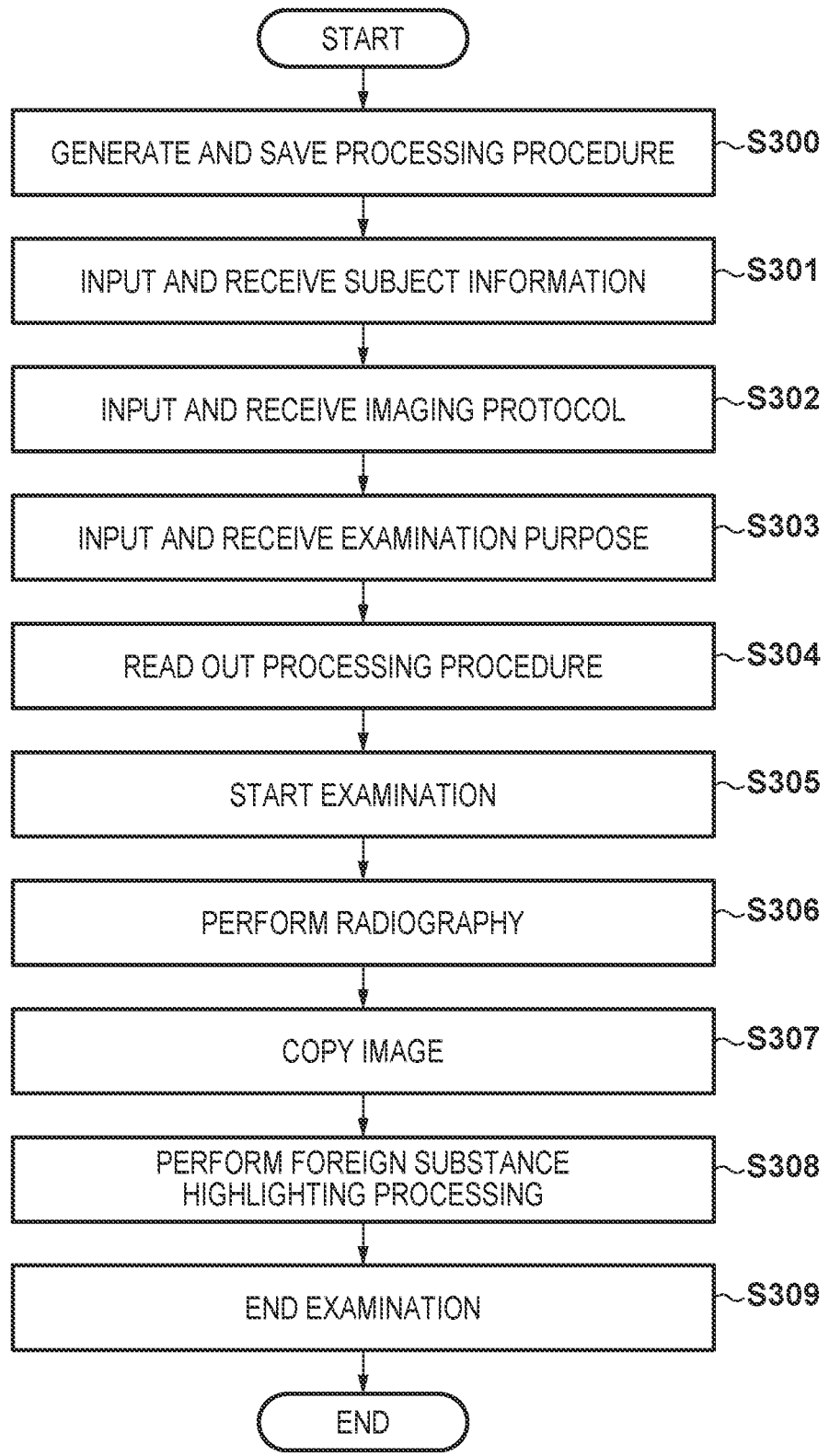

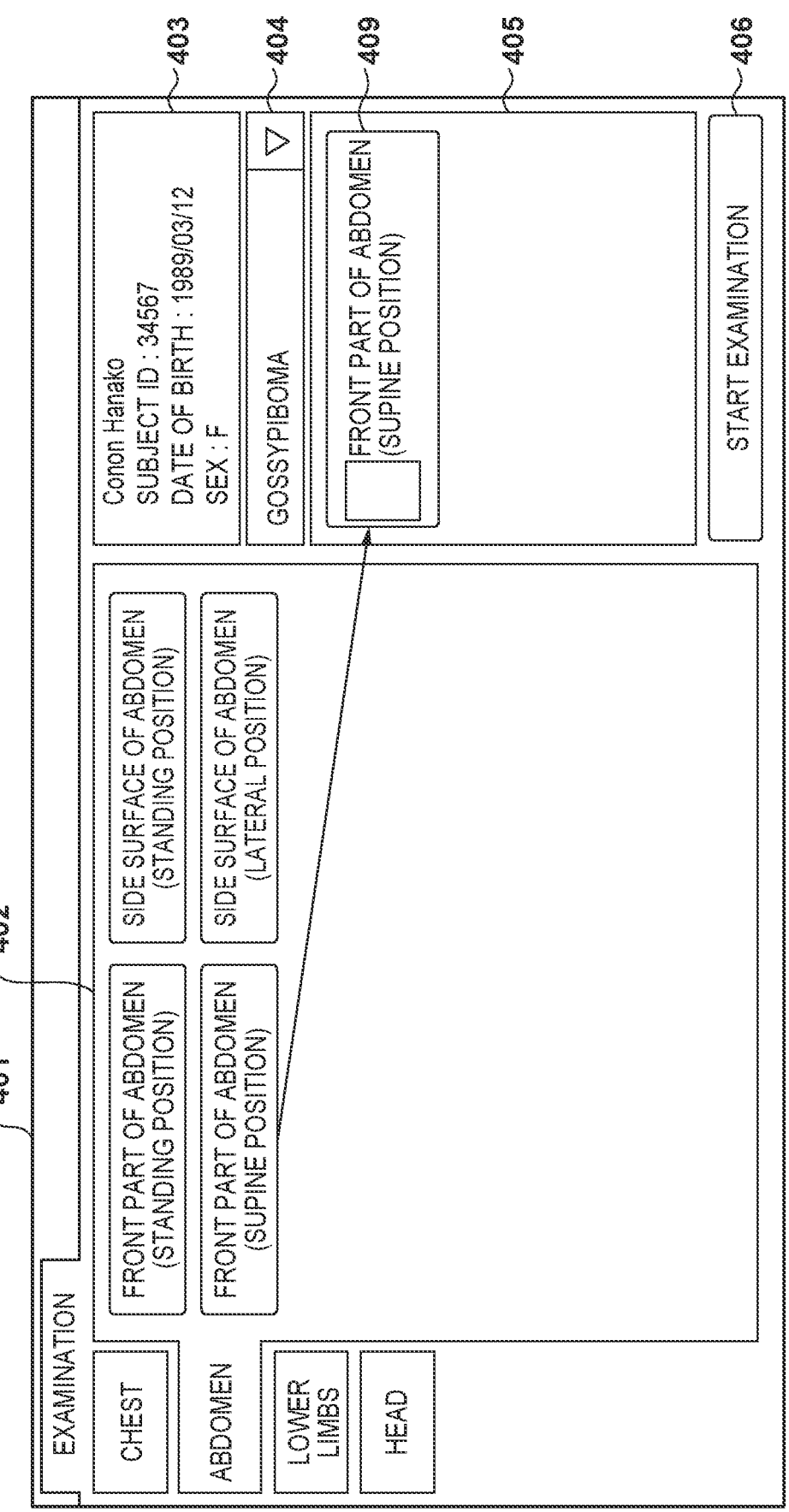

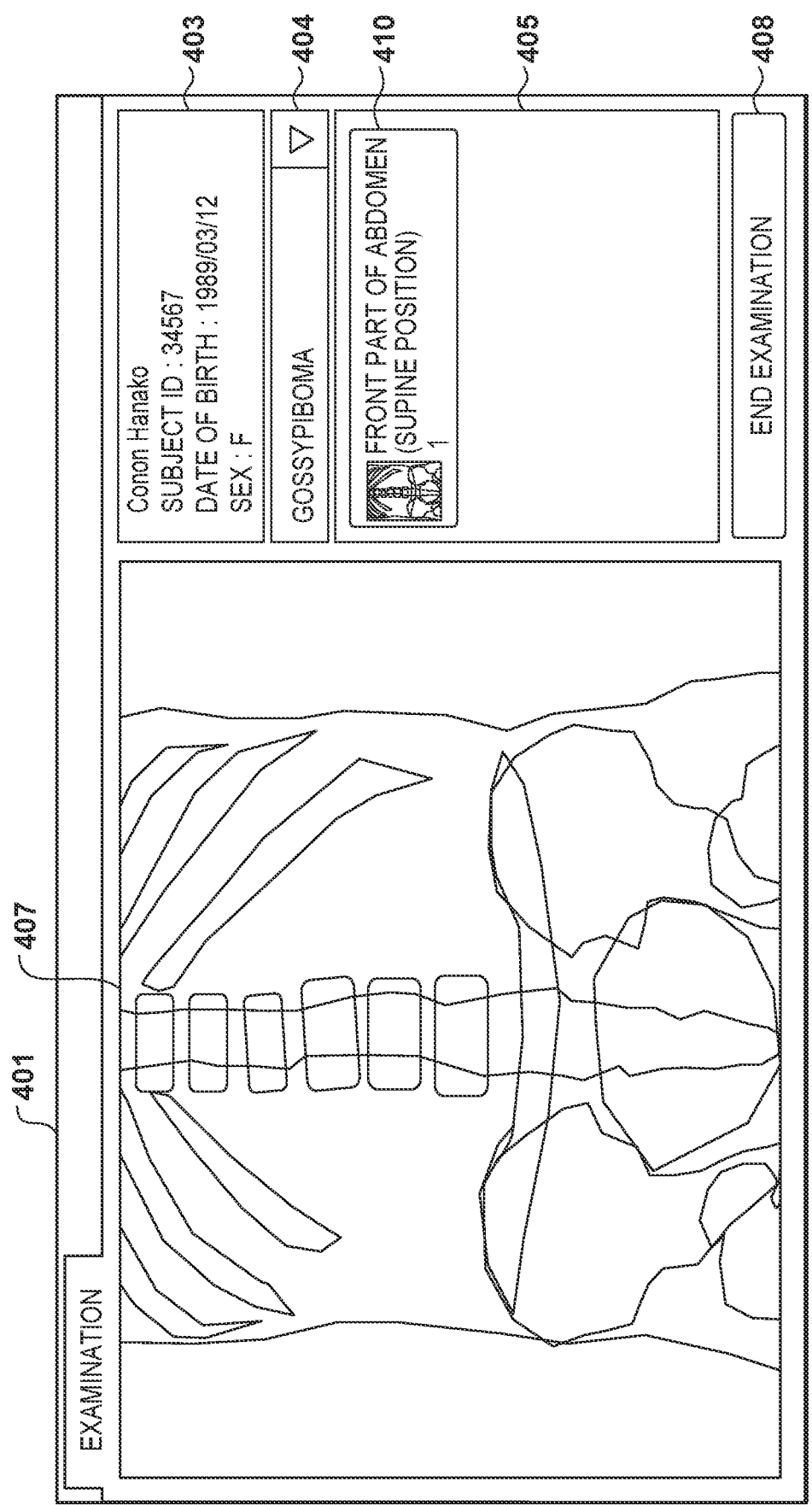

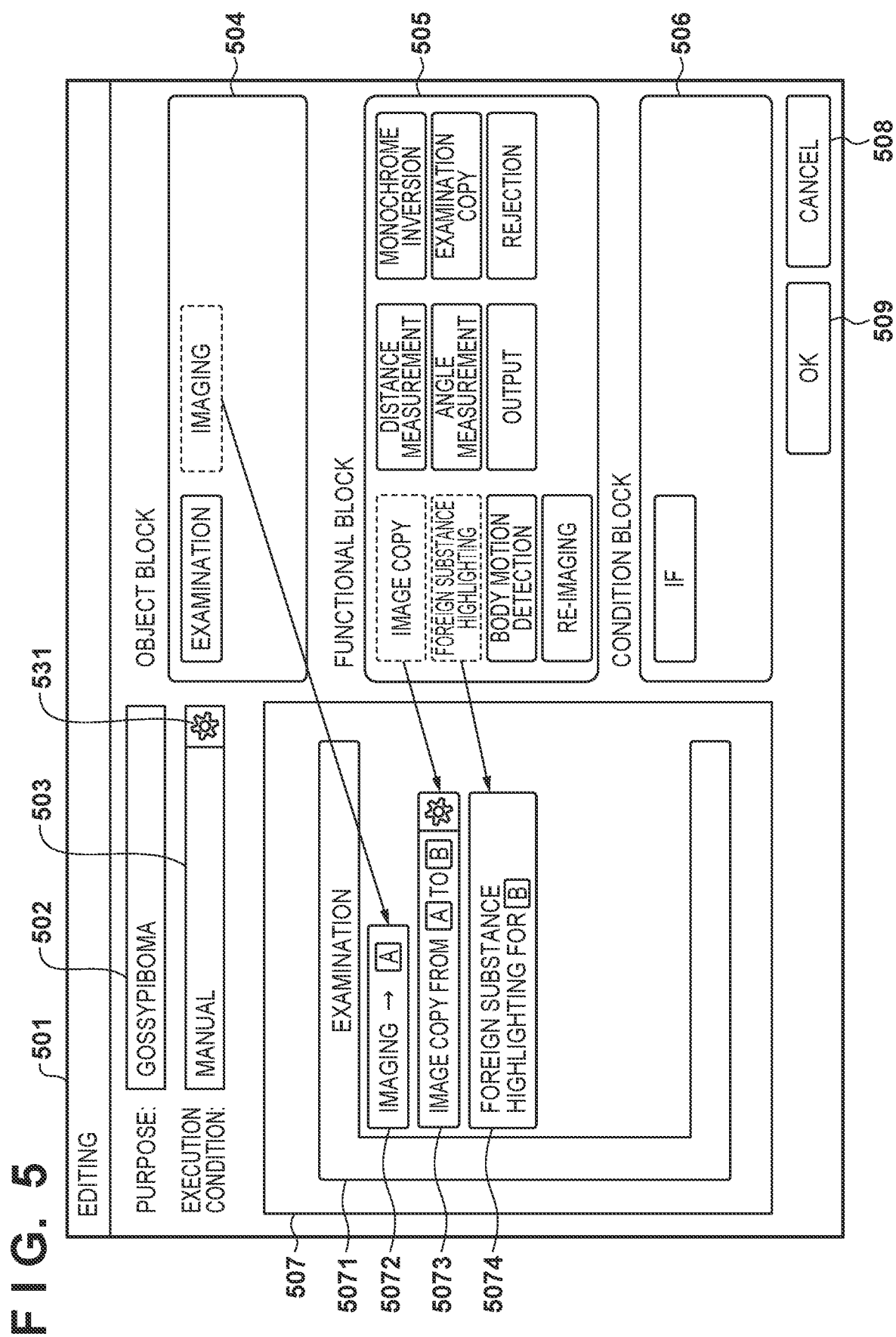

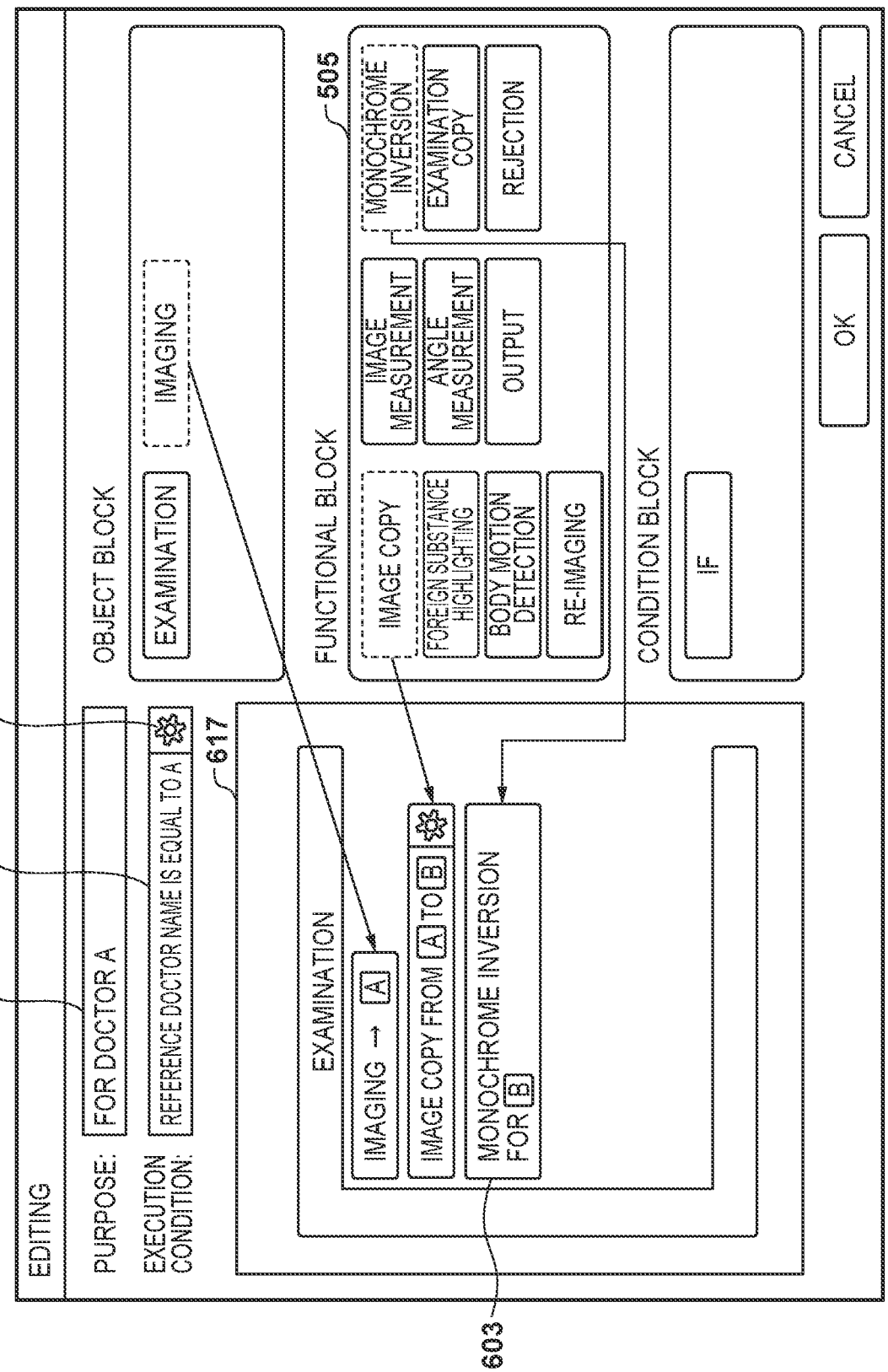

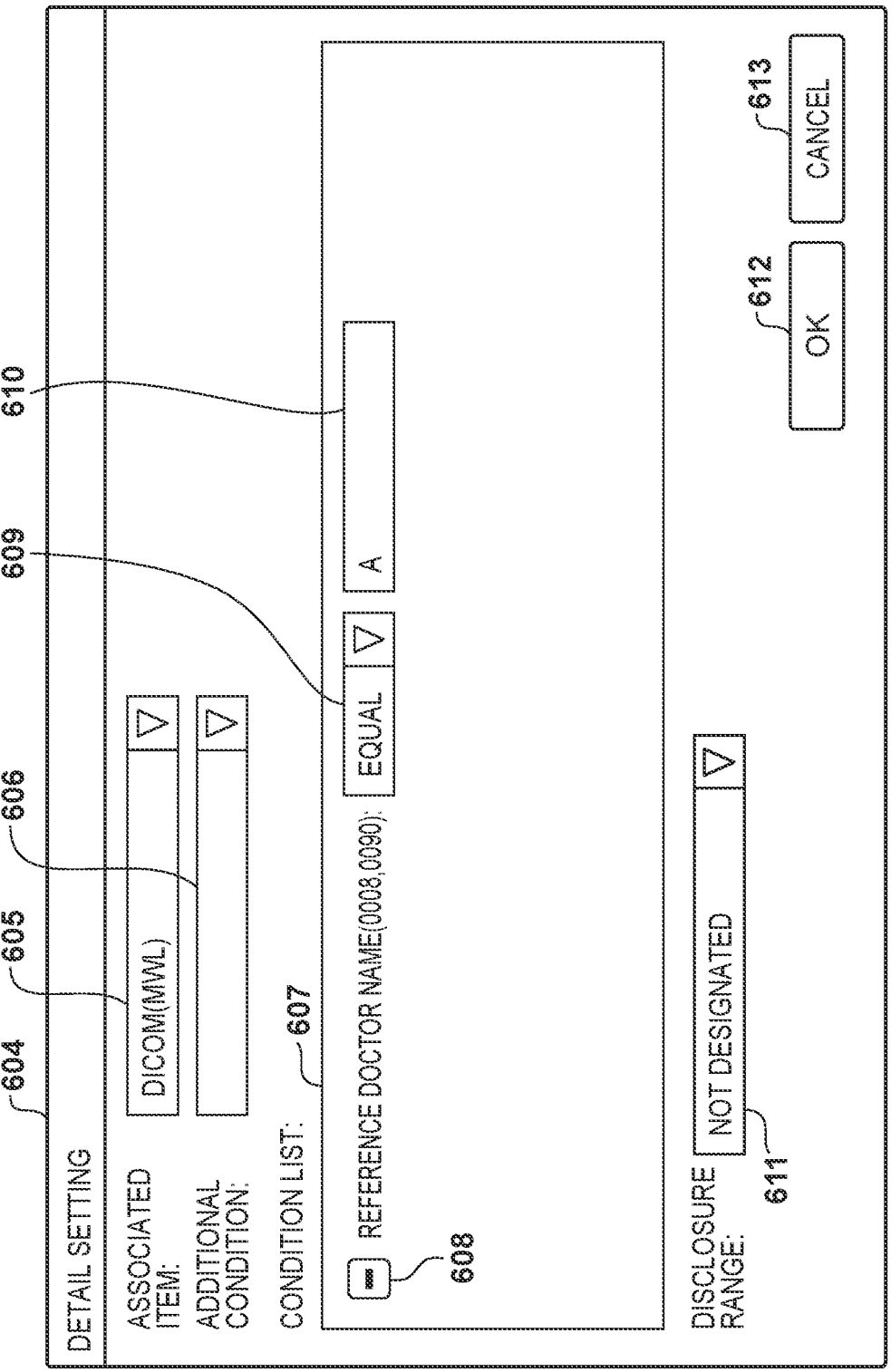

FIG. 7A

EDITING

PURPOSE: FRONT PART OF CHEST, OPERATOR Y

EXECUTION CONDITION: PROTOCOL IS FRONT PART OF CHEST AND OPERATOR ID IS Y

701

EXAMINATION
- IMAGING → [A]
- IMAGE COPY FROM [A] TO [B]
- IMAGE PROCESSING OF [LUNG FIELD] FOR [B]
- IMAGE COPY FROM [A] TO [C]
- IMAGE PROCESSING OF CATHETER TIP ENHANCEMENT FOR [C]
- IMAGE COPY FROM [A] TO [D]
- IMAGE PROCESSING OF [MEDIASTINUM] FOR [D]

703
704
705

702

OBJECT BLOCK
- EXAMINATION
- IMAGING

FUNCTIONAL BLOCK  505
- IMAGE COPY
- FOREIGN SUBSTANCE HIGHLIGHTING
- BODY MOTION DETECTION
- RE-IMAGING
- IMAGE PROCESSING
- ANGLE MEASUREMENT
- OUTPUT
- MONOCHROME INVERSION
- EXAMINATION COPY
- REJECTION

CONDITION BLOCK
- IF

OK     CANCEL

FIG. 7B

DETAIL SETTING

ASSOCIATED ITEM: OPERATOR ▽ — 706

ADDITIONAL CONDITION: ▽ — 707

CONDITION LIST: — 708

- PROTOCOL NAME: EQUAL ▽ FRONT PART OF CHEST
- OPERATOR ID: EQUAL ▽ UserY

DISCLOSURE RANGE: ONLY FOR MYSELF ▽ — 709

OK   CANCEL

F I G. 9
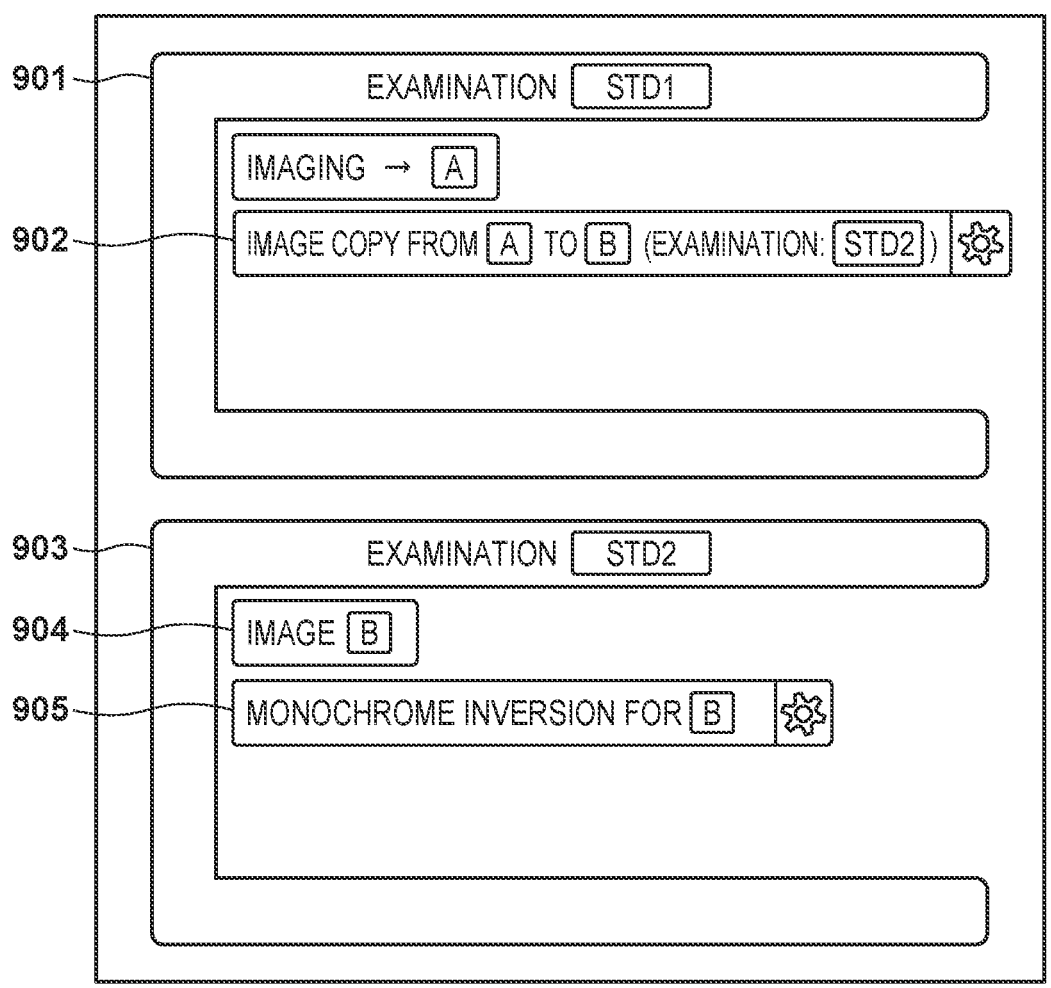

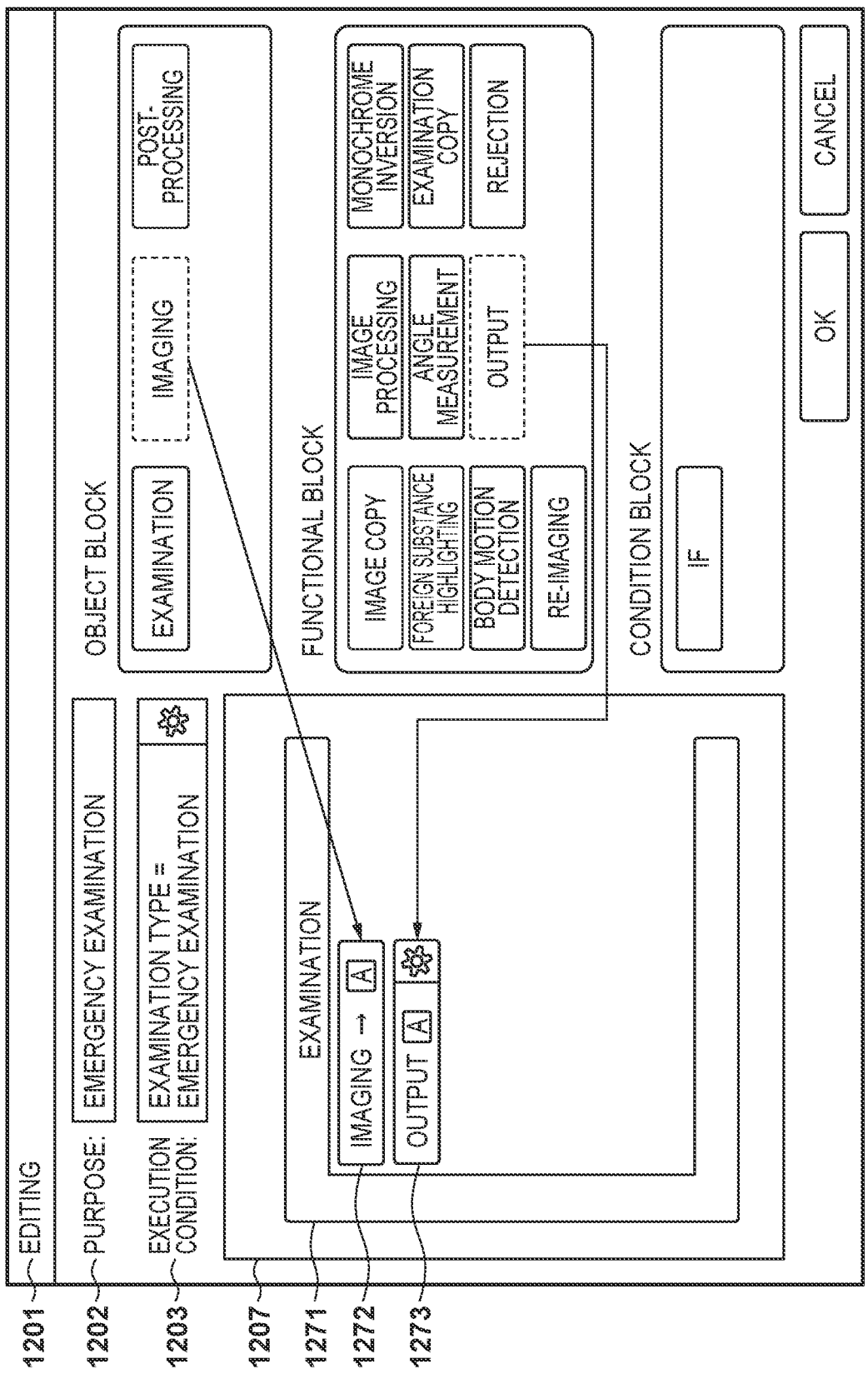

INFORMATION PROCESSING APPARATUS, RADIOGRAPHING APPARATUS, RADIOGRAPHING SYSTEM, INFORMATION PROCESSING METHOD, AND STORAGE MEDIUM

BACKGROUND OF THE INVENTION

Field of the Invention

The present invention relates to an information processing apparatus, a radiographing apparatus, a radiographing system, an information processing method, and a storage medium.

Description of the Related Art

Japanese Patent Laid-Open No. 2003-284709 discloses a technique of reading a code for specifying an imaging technique and performing radiography based on the imaging portion and direction requested by the specified imaging technique upon reception of examination information from a RIS (Radiology Information Systems). In radiography, an operator specifies the imaging portion and the imaging direction based on the examination information and performs radiography of a radiation image requested from a request source.

However, the examination information includes an instruction for an image as a result and does not include information indicating which image processing is performed to obtain an image. For this reason, if the operator judges different processing procedures depending on the examination purpose and the request source to prepare a requested image, the work load on the operator can increase.

SUMMARY OF THE INVENTION

An aspect of the present invention provides a technique capable of reducing the work load on an operator by processing a radiation image in accordance with preset processing procedures corresponding to an examination purpose.

According to one aspect of the present invention, there is provided an information processing apparatus comprising: a purpose setting unit configured to set an examination purpose of radiography; a selection setting unit configured to select processing of a radiation image corresponding to the examination purpose and set the processing in an editing area of a display unit; and a generation unit configured to generate a processing procedure corresponding to the examination purpose based on the set processing.

According to another aspect of the present invention, there is provided a radiographing apparatus comprising: a purpose determination unit configured to determine an examination purpose by radiography; a readout unit configured to read out a processing procedure corresponding to the examination purpose; an imaging unit configured to obtain a radiation image of radiation passing through a subject; and an execution unit configured to perform processing of the radiation image based on the processing procedure.

According to still another aspect of the present invention, there is provided a radiographing system comprising: a purpose determination unit configured to determine an examination purpose by radiography; a readout unit configured to read out a processing procedure corresponding to the examination purpose; an imaging unit configured to obtain a radiation image of radiation passing through a subject; and an execution unit configured to perform processing of the radiation image based on the processing procedure.

According to yet another aspect of the present invention, there is provided an information processing method comprising: setting an examination purpose of radiography; selecting processing of a radiation image corresponding to the examination purpose and setting an editing area of a display unit; and generating a processing procedure corresponding to the examination purpose based on the set processing.

The present invention enables to reduce a work load on an operator by processing a radiation image in accordance with preset processing procedures corresponding to an examination purpose.

Further features of the present invention will become apparent from the following description of exemplary embodiments with reference to the attached drawings.

BRIEF DESCRIPTION OF THE DRAWINGS

FIG. 3 is a flowchart showing radiographing processing sequence according to the embodiment;

FIGS. 4A to 4C are views for explaining the GUI of a radiographing system;

FIG. 5 is a view for explaining the GUI of the radiographing system;

FIG. 6A is a view showing an example of an editing screen of an examination purpose;

FIG. 6B is a view showing a detail setting screen for setting the contents of an execution condition setting unit;

FIGS. 7A and 7B are views for explaining the GUI of the radiographing system;

FIG. 9 is a view showing a display example of an examination block in a processing editing field;

FIG. 12 is a view for explaining a GUI of the radiographing system.

DESCRIPTION OF THE EMBODIMENTS

The embodiments of the present invention will be exemplarily described in detail with reference to the accompanying drawings. The constituent elements described in the embodiments are merely examples, and the present invention is not limited by the individual embodiments to be described below. Note that the radiation includes α-rays, β-rays, γ-rays, and various kinds of particle beams in addition to radiation.

First Embodiment (Hardware Arrangement of Radiographing System)

Figure 1:
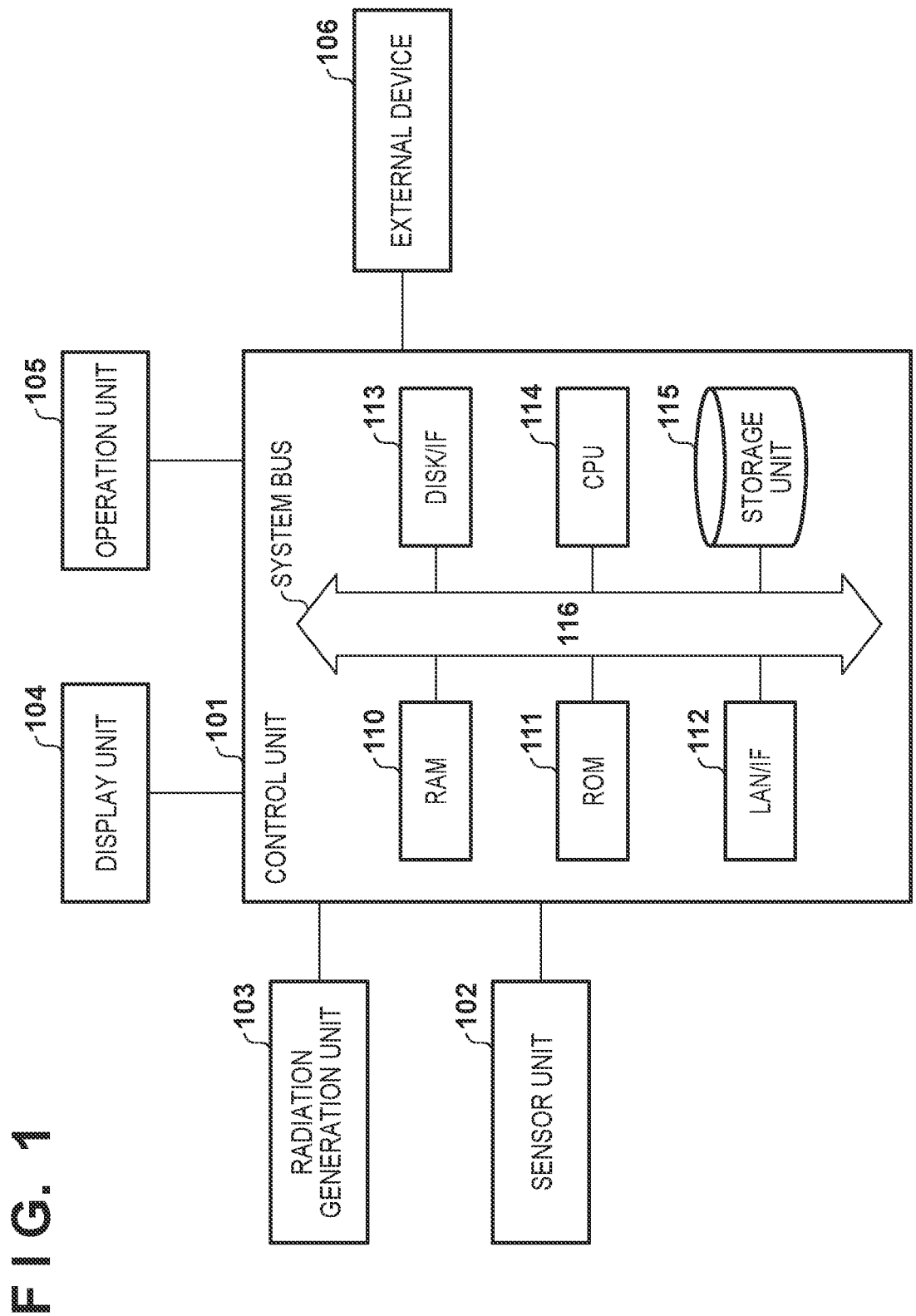
FIG. 1 is a block diagram showing the hardware arrangement of a radiographing system according to an embodiment.

FIG. 1 shows the hardware arrangement example of a radiographing system according to this embodiment. Note that the hardware arrangement of FIG. 1 is also referred to as a radiographing apparatus. As shown in FIG. 1, the radiographing system includes, for example, a control unit 101, a sensor unit 102, a radiation generation unit 103, a display unit 104, an operation unit 105, and an external device 106.

The control unit 101 controls driving of the sensor unit 102 and the radiation generation unit 103 based on input information by an operator. In addition, the control unit 101 functions as an information processing apparatus for managing sensor correction data for correcting data output from the sensor unit 102 and various kinds of data such as a radiographing condition and image data.

As a computer arrangement, the control unit 101 includes, for example, a RAM 110, a ROM 111, a LAN/IF 112, a DISK/IF 113, a CPU 114, and a nonvolatile storage unit 115 such as a hard disk. These hardware components are connected to each other via a system bus 116.

The sensor unit 102 has an arrangement in which pixels each including a switch element such as a TFT and a photoelectric conversion element are arranged two-dimensionally (for example, a two-dimensional array). For example, a phosphor element for converting radiation into visible light is formed on each photoelectric conversion element.

Radiation emitted from the radiation generation unit 103 to the sensor unit 102 is converted into visible light by the phosphor element. The converted visible light enters the photoelectric conversion element of each pixel. In each photoelectric conversion element, charge (an electrical signal) corresponding to the visible light is generated as radiation image data. The driving timing of the sensor unit 102 is controlled by the control unit 101, and the radiation image data generated by each photoelectric conversion element is transferred to the control unit 101.

The radiation generation unit 103 is a device for emitting radiation to a subject and the sensor unit 102 based on irradiation control by the control unit 101. The radiation generation unit 103 emits radiation in accordance with the signal from the control unit 101, and the radiation emitted from the radiation generation unit 103 is detected by the sensor unit 102 synchronized with the irradiation timing.

The display unit 104 is formed from, for example, a monitor such as a CRT or a liquid crystal display and displays image data, a GUI (Graphical User Interface), and the like on the screen.

The operation unit 105 is made from input devices such as a mouse, a keyboard, and an irradiation switch and is used to allow the user to input various kinds of commands and data to the control unit 101 and the GUI of the display unit 104. Note that a monitor having the functions of the display unit 104 and the operation unit 105 like a touch panel can be used.

The external device 106 represents a general DICOM (Digital Imaging and Communications in Medicine)-communicable external system such as a RIS (Radiology Information Systems), a PACS (Picture Archiving and Communication Systems) for saving and displaying radiographed image, and a DICOM viewer.

(Functional Arrangement of Control Unit 101)

Next, the functional arrangement example of the control unit 101 will be described with reference to FIG. 2. Note that the following description will exemplify that each functional unit is implemented as a function of the control unit 101. However, at least some of these functions may be implemented by other devices in the radiographing system.

Figure 2:
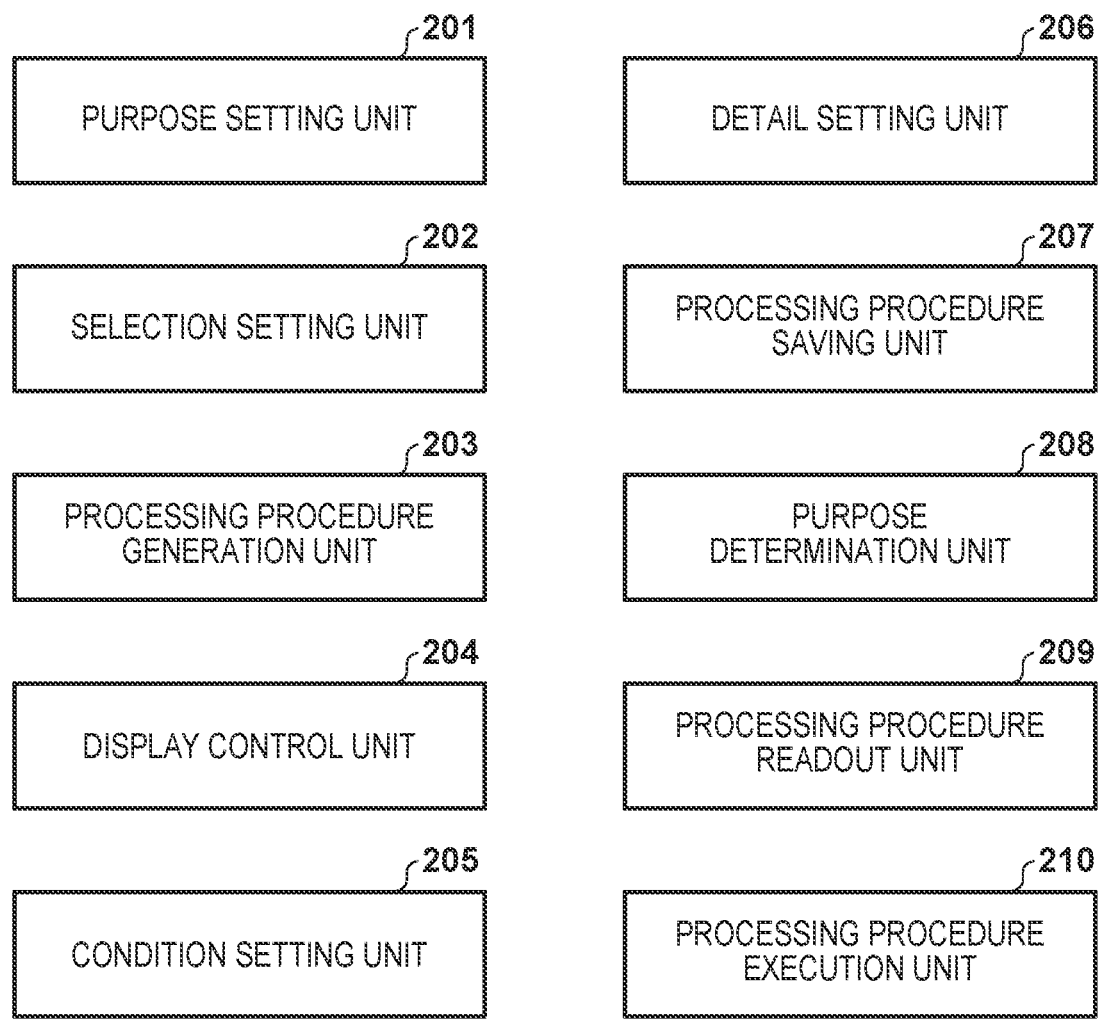
FIG. 2 is a block diagram for explaining the functional arrangement of a control unit according to the embodiment.

FIG. 2 is a block diagram showing the functional arrangement of the control unit 101. By executing the control programs stored in the nonvolatile storage unit 115, the control unit 101 functions as a purpose setting unit 201, a selection setting unit 202, a processing procedure generation unit 203, a display control unit 204, a condition setting unit 205, a detail setting unit 206, a processing procedure saving unit 207, a purpose determination unit 208, a processing procedure readout unit 209, and a processing procedure execution unit 210.

The purpose setting unit 201 performs processing for setting an examination purpose of radiography based on inputs from the GUI displayed on the display unit 104. For example, when the operator inputs an examination purpose of radiography to the purpose input field (for example, 502 in FIG. 5) of the GUI, the purpose setting unit 201 sets the examination purpose of radiography based on the input result of the purpose input field of the GUI. The purpose setting unit 201 can set the examination purpose from a list of examination purposes on the GUI. Alternatively, the purpose setting unit 201 can set the examination purpose of radiography based on the input from the GUI displayed on the display unit 104 or examination request source information included in the examination information received from the external device 106.

The examination purpose of radiography, which is set by the processing of the purpose setting unit 201 is saved in the nonvolatile storage unit 115 in association with the processing procedure to be described later. When executing the processing procedure, the processing procedure readout unit 209 reads out the processing procedure based on the purpose determined by the purpose determination unit 208. The processing procedure execution unit 210 executes the readout processing procedure.

The selection setting unit 202 selects radiation image processing corresponding to the examination purpose of radiography and sets the radiation image processing in the editing area of the display unit 104. More specifically, the selection setting unit 202 selects radiation image processing corresponding to the examination purpose of radiography from the display areas (for example, 504, 505, and 506 in FIG. 5) of the display unit 104 and sets the selected processing in the editing area (for example, 507 in FIG. 5) of the display unit 104.

Various kinds of items are displayed in the display areas of the display unit 104. The selection setting unit 202 selects image processing from the items displayed in the display area of the display unit 104 as radiation image processing and sets it in the editing area of the display unit 104. The selection setting unit 202 performs processing based on, for example, a drag-and-drop operation of the operation unit 105 by the operator. When the operator selects (drags) processing (block) displayed in the display area of the display unit 104 in accordance with an operation of the operation unit 105 and sets (drops) the selected processing in the editing area of the display unit 104, radiation image processing corresponding to the examination purpose of radiography is set in the editing area of the display unit 104. The selection setting unit 202 can select image processing from the display area as the radiation image processing and set it in the editing area.

The processing procedure generation unit 203 generates a processing procedure corresponding to the examination purpose of radiography based on processing set in the editing area of the display unit 104. If a plurality of pieces of radiation image processing are set in the editing area of the display unit 104, the processing procedure generation unit 203 generates a series of processing procedures for performing these pieces of the radiation image processing based on a combination of the plurality of pieces of set processing.

The display control unit 204 controls the display of the GUI of the display unit 104. For example, based on setting values input by the operator, the display control unit 204 can change the display of the GUI or display a setting screen for performing detail condition settings on the display unit 104. In addition, the display control unit 204 can perform display control for changing the display of selectable processing in the display area of the display unit 104 in accordance with the examination purpose of radiography set by the purpose setting unit 201. For example, selectable processing candidates can be stored in the nonvolatile storage unit 115, processing corresponding to the examination purpose of radiography can be read out from the nonvolatile storage unit 115, and the readout processing can be displayed in the display area of the display unit 104.

The condition setting unit 205 sets a processing procedure execution condition based on information of an examination request source. For example, the condition setting unit 205 makes examination request source information (for example, information indicating the doctor name of the requesting department) included in the examination information received from the RIS cooperate with the examination purpose and sets a processing procedure execution condition. The condition setting unit 205 can set identification information of a user and the disclosure range of the generated processing procedure as the processing procedure execution conditions.

The detail setting unit 206 can set the details of processing set in the editing area of the display unit 104. For example, when generating copied images of radiation images as image processing, the detail setting unit 206 can set a hierarchical structure for storing copied images as an image generation condition in accordance with a radiogram interpretation order on the side of the external device.

The processing procedure saving unit 207 is a functional block for saving the processing procedure generated by the processing procedure generation unit 203 in the nonvolatile storage unit 115.

The purpose determination unit 208 is a functional block for determining an examination purpose of radiography to be performed. The purpose determination unit 208 can determine the examination purpose of radiography based on an input from the GUI. For example, the purpose determination unit 208 can determine the examination purpose from a list of examination purposes on the GUI. In addition, the purpose determination unit 208 can determine the examination purpose based on examination request source information included in the examination information received from the external device 106. For example, the purpose determination unit 208 can obtain the examination purpose information from the examination information received from the RIS and automatically determine the examination purpose of radiography.

The processing procedure readout unit 209 is a functional block for reading out a processing procedure from the nonvolatile storage unit 115 in accordance with the examination purpose determined by the purpose determination unit 208. The processing procedure execution unit 210 is a block for executing various kinds of processing procedures in accordance with the processing procedures read out by the processing procedure readout unit 209. The DISK/IF 113 shown in FIG. 1 functions as an obtaining unit for obtaining examination information from an external. The processing procedure execution unit 210 performs radiation image processing based on the processing procedure corresponding to the examination purpose included in the examination information obtained by the DISK/IF 113 (obtaining unit).

(Sequence of Radiography Processing)

Next, the sequence of radiography processing according to this embodiment will be described below. By using, for example, the GUIs shown in FIGS. 5 to 12, various kinds of processing procedures are generated based on processing operations of the purpose setting unit 201, the selection setting unit 202, the processing procedure generation unit 203, the display control unit 204, the condition setting unit 205, the detail setting unit 206, and the processing procedure saving unit 207 in correspondence with the examination purposes in radiography. The generated processing procedures are stored in the nonvolatile storage unit 115.

When performing an examination in radiography shown in FIG. 3, the purpose determination unit 208 determines an examination purpose of radiography to be performed from now on. In this case, the purpose determination unit 208 can determine the examination purpose based on the examination purpose information included in the examination information received from the RIS functioning as the external device 106. The processing procedure readout unit 209 reads out the processing procedure corresponding to the examination purpose determined by the purpose determination unit 208. The radiographing apparatus obtains a radiation image of radiation passing through the subject, and the processing procedure execution unit 210 performs radiation image processing based on the processing procedure read out by the processing procedure readout unit 209.

FIG. 3 is a flowchart for explaining the examination sequence in radiography according to this embodiment and shows the procedures from the input of the subject information to the end of the examination. Note that for easy understanding, a description will be made based on a more specific case (a radiation examination for confirming the presence/absence of a hemostatic gauze after a laparotomy). Before the start of execution of the radiographing processing sequence to be described below, the processing procedure corresponding to the confirming radiation examination is set in advance as the processing procedure of an examination purpose of a "gossypiboma" (a method of setting the specific processing procedure using a GUI will be described later in detail).

In step S300, before the radiographing examination, a processing procedure is generated and saved in the nonvolatile storage unit 115. Based on the GUI inputs shown in FIGS. 5 to 12 to be described later, the purpose setting unit 201, the selection setting unit 202, the processing procedure generation unit 203, the display control unit 204, the condition setting unit 205, the detail setting unit 206, and the processing procedure saving unit 207 perform processing to generate various kinds of processing procedures corresponding to the set examination purpose. The generated processing procedures are saved in the nonvolatile storage unit 115.

In step S301, subject information is input. The subject information such as identification information (ID), name, sex, and date of birth, and the like of the subject to be subjected to an examination is input. The subject information can be input by various kinds of methods such as reading of an ID card and the input using the examination information from the RIS in addition to the manual input by the operator. Any method can be used if the subject information can be input.

In step S302, an imaging protocol is determined. Pieces of information necessary for imaging such as the imaging portion and direction, the radiation condition, and the image processing condition are associated with each other in advance and packaged in the imaging protocol. The operator selects an imaging protocol by clicking, with a mouse, a desired imaging protocol from a list of imaging protocols displayed on the GUI. Assume that in this embodiment, an imaging portion "front part of abdomen (supine position)" is selected.

In step S303, an examination purpose of radiography to be performed is determined. For example, the operator inputs a desired examination purpose in the GUI purpose input portion and selects a desired examination purpose from the list of examination purposes displayed on the GUI. This makes it possible for the purpose determination unit 208 to determine the examination purpose of radiography. The purpose determination unit 208 can obtain examination purpose information from the examination information received from the RIS to automatically set the examination purpose.

In step S304, the processing procedure readout unit 209 reads out the preset processing procedure based on the examination purpose determined in step S303. The processing procedures are stored in the nonvolatile storage unit 115 in correspondence with various kinds of examination purposes. The processing procedure readout unit 209 reads out the processing procedure associated with the determined examination purpose from the nonvolatile storage unit 115.

For example, if the operator inputs the examination purpose "gossypiboma" on the GUI in the purpose input portion in step S303, the processing procedure readout unit 209 reads out the processing procedure associated with this purpose from the database or the like of the nonvolatile storage unit 115. Assume that the readout processing procedure is a processing procedure "foreign substance highlighting processing after the radiographed image is copied" by the generation processing of the processing procedure generation unit 203. This processing procedure includes processing "copy the radiographed image" and processing for performing "the foreign substance highlighting processing" for the copied image data. These two kinds of processing set in this case (processing procedures) are executed by step S307 (image copy) and step S308 (foreign substance highlighting processing) to be described later. Note that processing operations from step S301 to step S303 need not always be executed in the order shown in FIG. 3, provided that these pieces of information are input before the start of the examination.

In step S305, if the operator clicks the examination start button to send an examination start instruction to the radiographing system, the radiographing system starts the examination. Note that the readout of the processing procedure in step S304 may be executed after step S305 or may be performed at any timing before the actual radiography. If the examination is started, the control unit 101 sets the sensor unit 102 in an imaging enable state to perform imaging at the "front part of abdomen (supine position)" input in step S302. The control unit 101 sets the sensor unit 102 in the imaging enable state and the radiation generation condition for the radiation generation unit 103.

If the imaging preparation is complete and an irradiation enable state is set, the operator presses the irradiation switch to cause the radiation generation unit 103 having received the irradiation start signal to emit the radiation in step S306. The radiation passing through the subject is converted into radiation image data by the sensor unit 102, and the radiation image data is transferred to the control unit 101. The radiation image data transferred to the control unit 101 is displayed on the display unit 104.

In step S307, based on the processing procedure read out in step S304, the processing procedure execution unit 210 copies the radiation image data obtained in step S306. The copy processing of the radiation image data corresponds to the "copy the radiographed image" out of the processing procedure "perform foreign substance highlighting processing after the radiographed image is copied" associated with the examination purpose.

After that, in step S308, the processing procedure execution unit 210 performs foreign substance highlighting processing for the radiation image data copied in step S307. This processing is also performed based on the processing procedure read out in step S304. The foreign substance highlighting processing corresponds to "the foreign substance highlighting processing is performed" out of the processing procedure "the foreign substance highlighting processing is performed after the radiographed image is copied" associated with the examination purpose.

Finally, in step S308, an abdomen image in which the foreign substance highlighting processing is performed so as to allow the operator to easily observe a foreign substance (gauze) in the body cavity of the subject is displayed on the display unit 104. If the image confirmation is complete and it is determined that subsequent imaging is unnecessary, the operator clicks the examination end button to end the examination in the radiographing system in step S309.

(Setting Example of Processing Procedure Using GUI)

Next, the GUIs in the radiographing system will be described. The control unit 101 can perform display control of various kinds of GUIs on the display unit 104. FIG. 4A is a view showing a GUI example of a screen on which an imaging portion and an imaging purpose are input before the start of the examination. An imaging protocol display area 402 is displayed in an application screen 401 of the display unit 104. The imaging protocols which can be used in this radiographing system are arrayed and displayed for each category in the imaging protocol display area 402. Information necessary for imaging such as an imaging portion (for example, a chest or abdomen), an imaging direction (for example, a standing position, a supine position, and a lateral position), a radiation condition, an image processing condition is associated in advance with each imaging protocol.

Figure 4C:
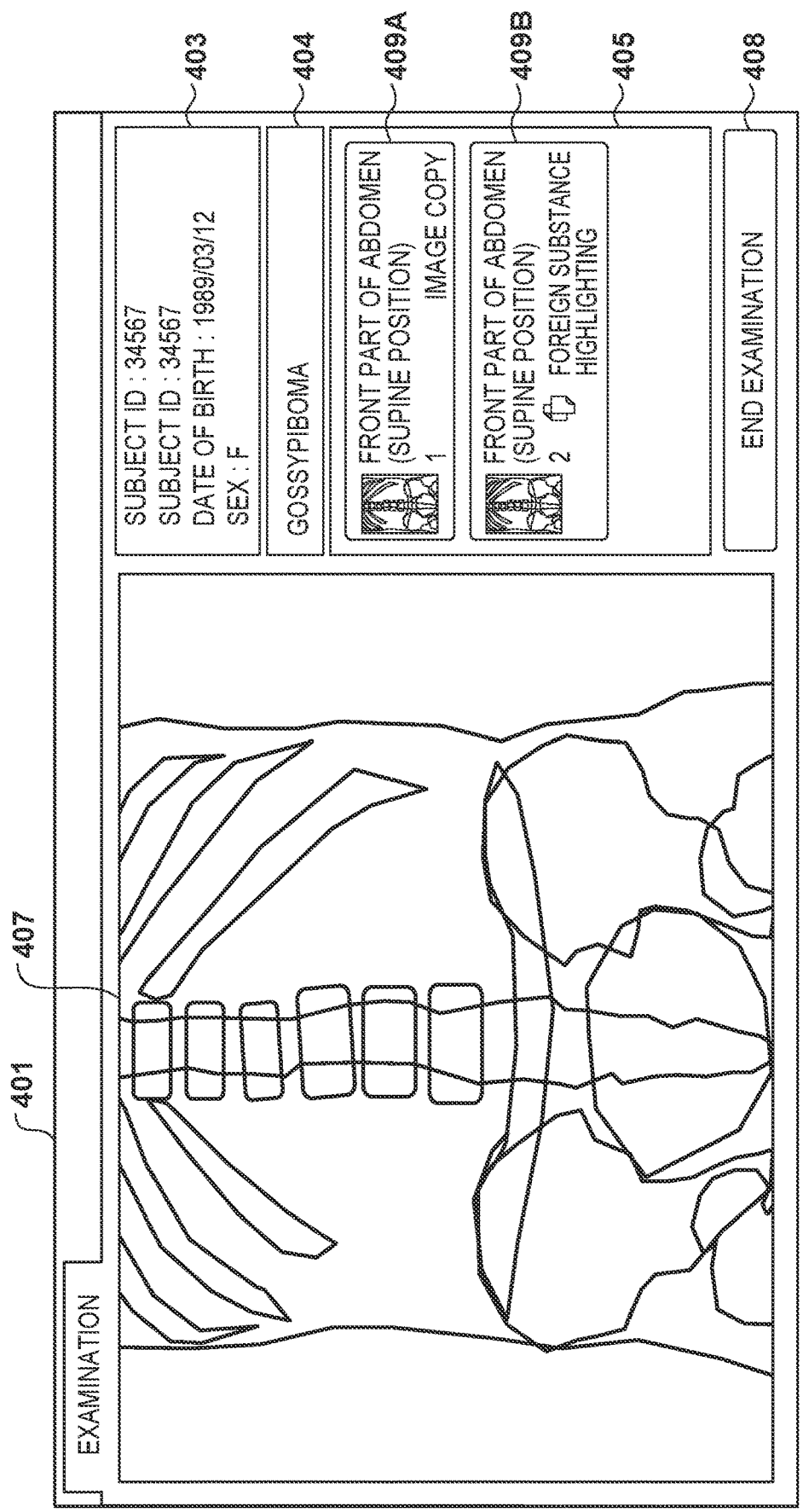

When the operator clicks and selects an imaging protocol displayed in the imaging protocol display area 402 by the operation unit 105, the imaging protocol for the subsequent radiography is selected. The selected imaging protocol is displayed in a display area 405. FIGS. 4A to 4C exemplarily show that one imaging protocol ("front part of abdomen (supine position)") is selected from the imaging protocol display area 402 and set in the display area 405.

In a subject information display area 403, for example, a subject name input on another screen (not shown), identification information (subject ID) for specifying the subject, the date of birth, the sex, and the like are displayed.

A setting area 404 is an examination purpose setting area. FIGS. 4A to 4C show that the examination purpose "gossypiboma" is selected from the list of purposes displayed on the list. A plurality of examination purposes are displayed in the form of a pull-down menu. The operator selects an examination purpose by a selection operation using the operation unit 105, thereby setting the examination purpose in the setting area 404.

The operator clicks an examination start button 406 by the operation unit 105 to cause the radiographing system to start the examination.

According to this embodiment, assume that as the processing procedure associated with the examination purpose, processing "the foreign substance highlighting processing is performed after the radiographed image is copied" is set.

FIG. 4B is a view exemplarily showing the screen of the display unit 104 after execution of imaging of the "front part of abdomen (supine position)" upon the start of the examination. The obtained radiation image data is displayed in an image display area 407. In a state after imaging, the control unit 101 sets an examination end button 408 in an invalid state and validates the examination end button 408 upon completion of the processing associated with the examination purpose. If the processing procedure associated with the examination purpose is not set, the control unit 101 sets the examination end button 408 in a valid state after imaging. When the operator clicks the examination end button 408 by the operation unit 105, the examination normally ends. Since all the processing (copy of the radiographed image and foreign substance highlighting processing) associated with the examination purpose is not completed at the timing when imaging ends and the screen in FIG. 4B is displayed is not completed, processing cannot end even if the operator clicks the examination end button 408.

FIG. 4C is a view exemplarily showing the screen of the display unit 104 after the processing procedure associated with the examination purpose ends. After imaging of the radiation image displayed in FIG. 4B, image copy is performed based on the processing procedure associated with the examination purpose "gossypiboma", and an image having undergone image processing after performing foreign substance highlighting processing for the copied image is displayed in the image display area 407.

Display 409A and display 409B of the respective processing procedures associated with the examination purpose are displayed in the display area 405. The processing procedure display 409A shows the processing procedure of image copying and corresponds to processing for copying the radiation image displayed in the image display area 407 of FIG. 4B.

The display control unit 204 can cause the display unit 104 to display a combination of a thumbnail image obtained by reducing the image processed based on the processing procedure and the text display indicating the contents of the processing procedure. The processing procedure display 409A displays a state of a combination of the icon display of the thumbnail image obtained by reducing the copied image and the text display ("image copy") indicating the specific processing procedure processing.

In addition, the processing procedure display 409B indicates the processing procedure of the foreign substance highlighting processing for the copied image. The processing procedure display 409B displays a state of a combination of the icon display of the thumbnail image obtained by reducing the image having undergone foreign substance highlighting and the text display ("foreign substance highlighting") indicating the specific processing procedure processing.

Note that if a processing procedure is set in advance, the control unit 101 can automatically performs a state transition from the display state of the radiographed image in FIG. 4B to the display state after image processing by the processing procedure in FIG. 4C based on the set processing procedure. After the end of the processing procedures associated with the examination purpose, the control unit 101 validates the examination end button 408. Accordingly, when the operator clicks the examination end button 408 by the operation unit 105, the examination can end.

(Setting Example of Examination Purpose and Processing Procedure)

Next, a method of setting the examination purpose and the processing procedure using the GUI will be described below.

FIG. 5 is a view showing an example of a GUI for setting the processing procedure. The display control unit 204 controls the display of the display unit 104 to display an editing screen 501 as a GUI. In the editing screen 501, the purpose input field 502 serves as an input area for setting an examination purpose. Information input to the purpose input field 502 can be used as information for allowing the operator to identify it as the label of the examination purpose.

An execution condition setting field 503 serves as an input area for setting a processing procedure execution condition. In the GUI in FIG. 5, "manual" indicating that the operator performs manual selection is set. A right end icon 531 of the execution condition setting field 503 plays a role of calling a sub-screen (not shown) for setting the execution condition. The contents selected on the sub-screen are set in the execution condition setting field 503.

Referring to FIG. 5, the object block display field 504, the functional block display field 505, and the condition block display field 506 form the display areas of the display unit 104. In addition, in FIG. 5, the processing editing field 507 forms the editing area of the display unit 104.

The object block display field 504 is an area for displaying processing corresponding to the purpose input in the purpose input field 502. In this case, "examination" and "imaging" are displayed in a selectable state as the purpose processing (blocks). Processing (block) selected by the drag-and-drop operation using the operation unit 105 such as a mouse is set in the processing editing field 507 as the processing corresponding to the purpose in the purpose input field 502. The example of FIG. 5 shows that imaging is selected and set in the processing editing field 507.

The functional block display field 505 is a display area for displaying various pieces of processing for an image such as image copy and foreign substance highlighting processing as one processing item (functional block). The processing item (functional block) selected by the drag-and-drop operation is set in the processing editing field 507 as the specific processing for the image. The example of FIG. 5 shows that the image copy and foreign substance highlighting are selected and set in the processing editing field 507.

The condition block display field 506 is a display area for displaying a condition branch processing block used when processing is branched based on a specific condition. In this case, "IF" is displayed as the condition branch processing block. Various condition branch processing blocks such as "IF_ELSE" can be displayed in the condition block display field 506 in addition to this. If a condition branch processing block is selected and set in the processing editing field 507, the processing procedure generation unit 203 generates a processing procedure for performing condition determination processing for a result of processing (functional block) selected from the functional block display field 505.

The processing editing field 507 is an editing area for setting a processing procedure in an examination and a work area for setting the contents of the processing procedure by causing the operator to perform a drag-and-drop operation for a block displayed in each of the object block display field 504, the functional block display field 505, and the condition block display field 506 by the operation unit 105.

An examination block 5071 expresses a series of processing procedures from the start to the end of one examination. Various blocks are arranged inside a square U-shaped figure, thereby setting the processing procedures in the examination. The processing procedure generation unit 203 generates a series of processing procedures for performing processing of a radiation image based on a combination of a plurality of set processing operations. In the example of FIG. 5, the processing procedures, that is, image copy and foreign substance highlighting as the image processing for a radiographed image A are generated.

If "imaging" is selected by a drag-and-drop operation as processing (block) from the object block display field 504, an imaging block 5072 is set in the processing editing field 507. The imaging block 5072 indicates that a name as A is assigned to the image obtained by imaging. Under the display control of the display control unit 204, the name A is set as a default name, and the operator can arbitrarily change the name using the operation unit 105.

If the "image copy" and "foreign substance highlighting" are selected from the functional block display field 505 by the drag-and-drop operations as the processing items (functional blocks), an image copy block 5073 and a foreign substance highlighting block 5074 are set in the processing editing field 507.

The image copy block 5073 indicates that the image is to be copied. If the image copy in the display area of the functional block display field 505 is dragged to the processing editing field 507, the display control unit 204 changes a GUI display form so as to allow the operator to input an image copy source and an image copy destination. The display example in FIG. 5 sets that the image A is copied as an image B. GUI display control can be performed for the copy source image "A" such that since only the image "A" is present before this processing block, the display control unit 204 automatically inputs the copy source image name "A" and the copied image name "B" from the viewpoint of operability.

The foreign substance highlighting block 5074 indicates that foreign substance highlighting processing is performed for the copied image B. If the foreign substance highlighting block in the display area of the functional block display field 505 is dragged to the processing editing field 507, the display control unit 204 changes the GUI display to a mode capable of performing foreign substance highlighting processing for a specific image. In this case, foreign substance highlighting processing is set to be performed for the image "B".

The display control unit 204 preferentially performs foreign substance highlighting processing for an immediately preceding image (the image B in the case of FIG. 5) and can perform default setting of the immediately preceding image as the purpose image of foreign substance highlighting processing.

The examination block 5071 expresses a processing procedure loop that is repeatedly performed in the examination. The imaging block 5072 indicates each individual imaging in the examination. That is, if there are two imaging requests, that is, the front part of the chest and the side part of the chest in an examination order, the imaging block 5072 is set in the mode for performing the imaging operations for these requests. If the processing procedure shown in FIG. 5 is set, foreign substance highlighting is performed for all images to be obtained in the examination.

Assume that the operator wants to change processing depending on the imaging portion in the setting of the foreign substance highlighting block 5074. In this case, it is possible to arrange a condition block by a drag-and-drop operation to set a condition such as "a case in which the imaging portion of the image A is the front part of the chest", thereby generating a processing procedure for branching the processing. A use example of a condition block will be described later.

If a cancel button 508 is clicked by the operation unit 105 such as a mouse, the display control unit 204 controls the display of the display unit 104 to discard the editing contents of the editing screen 501 and then close the editing screen 501. On the other hand, if an OK button 509 is clicked by the operation unit 105 such as a mouse, the display control unit 204 saves the editing contents of the editing screen 501 and then closes the editing screen 501.

As has been described above, according to this embodiment, a radiation image is processed in accordance with a processing procedure set in advance, thereby reducing the work load on the operator. Since various kinds of processing operations required in accordance with the purpose can be processed by the processing procedures set in advance, there is provided a radiographing technique excellent in convenience because cumbersome routine work is not forced to the operator.

Second Embodiment

The first embodiment has described the arrangement for manually inputting processing purpose settings. However, the processing purpose (examination purpose) can be cooperated with examination request source information included in the examination information received from the RIS. As such an embodiment, an example for making an examination purpose cooperate with a doctor name of a requesting department will be described below.

The departments which make requests for examinations in a hospital are various departments such as an internal medicine department, a respiratory department, and an orthopedic department, and doctors who make requests are various doctors. For example, when performing radiogram interpretation of an image of the front part of a chest, some doctors want to refer to a monochrome-inverted image in addition to a normal image, and some doctors do not want a monochrome-inverted image.

Normally, examination information includes only request information for a radiation image to be obtained. No request is made for an image having undergone another image processing based on the radiographed image. That is, in this embodiment, information indicating that one image of the "front part of the chest" is to be captured is notified as the examination information.

On the other hand, the examination information can include a request source doctor name. For example, reference information called Referring Physician's Name exists in the Modality Worklist notified by a DICOM protocol. It is possible to notify the name of a doctor who refers to an examination result. By associating this reference information with an examination purpose, the examination purpose can be automatically selected from the received examination information. That is, a radiographed image is copied and its monochrome-inversion is set in advance as the processing procedure for the "doctor A". This makes it possible to automatically perform specific processing for the radiographed image such that a monochrome-inverted copied image is generated for the doctor name of the requesting department.

FIG. 6A is a view showing an example of an examination purpose editing screen used in this embodiment. In this embodiment, only differences from FIG. 5 will be described in order to avoid redundancy.

A character string "for doctor A" is input as an examination purpose in the input area of a purpose input field 601. A condition "reference doctor name is equal to A" is input in an execution condition setting field 602. The monochrome-inverting in the display area of a functional block display field 505 (FIG. 5) is selected by a drag-and-drop operation and a monochrome inversion processing block 603 is set in an editing area 617. Processing for monochrome-inverting an image B obtained by copying a radiographed image A is set in the monochrome inversion processing block 603.

FIG. 6B shows the detail setting screen of an execution condition for setting the contents of the execution condition setting field 602. If a right side icon 615 of the execution condition setting field 602 is clicked by an operation unit 105 such as a mouse, a display control unit 204 controls the display of a display unit 104 to display a detail setting screen 604 of the execution condition as a sub-screen GUI. An item is associated with the examination purpose, its condition, a disclosure range, and the like can be set in the detail setting screen 604.

An associated item selection field 605 indicates association with a DICOM modality worklist (to be also referred to as a DICOM(MWL)) received from the RIS. In the display of an additional condition selection field 606, a selection choice is changed depending on the selection of the associated item selection field 605. For example, if the association with the DICOM(MWL) is selected, a DICOM tag can be selected from the list of DICOM tags included in the examination information received from the RIS. For example, in a specific use case, if an associated item is selected, an additional condition list corresponding to the selected item is automatically opened, so that the operator as the user can select a desired condition from the additional condition list corresponding to the item. For example, information concerning the doctor of the request source can also be selected.

The associated items selectable in the associated item selection field 605 include, for example, user information, subject information, imaging portion, examination type, examination time, and the like in addition to the DICOM (MWL) shown in this embodiment. The associated items are not limited to the examples shown in this embodiment. For example, if subject information includes smoking history information, image processing suitable for rendering a lung field nodule is possible as an additional imaging portion.

A condition list display area 607 is a display area for displaying a condition selected in the additional condition selection field 606. In this case, a condition representing that "reference doctor name (0008, 0090) (each value in the parentheses indicates the DICOM tag number) out of the information received by the DICOM modality worklist is equal to "A" is added. Note that in FIG. 6B, the display of the additional condition selection field 606 is kept empty (blank) because the state is a state immediately after the additional condition selection. If the operator wants to add a plurality of conditions, the additional condition selection field 606 can be opened again to select a desired condition.

If a condition deletion button 608 is clicked by a mouse or the like, a condition can be removed from the condition list of the condition list display area 607. A condition selection field 609 designates a condition to be compared with the received reference doctor name. In this case, the condition "equal" is set, but any other condition such as "larger than", "smaller than", "equal to or larger than", "equal to or smaller than", or "not preferable" can be set. An evaluation value input field 610 is an input area for inputting a value for evaluating a condition set by the condition selection field 609. In this embodiment, in order to set the condition "reference doctor name is A", "A" is input as the evaluation value. A condition setting unit 205 sets a processing procedure execution condition based on examination request source information included in the examination information received from the RIS.

A disclosure range setting field 611 can set a range in which this setting is disclosed. In the example of FIG. 6B, the disclosure range is not limited, that is, "no designation" is set. However, for example, the disclosure range can be limited to the operator who has created this setting or to a group to which the operator belongs. If an OK button 612 is clicked by a mouse or the like, the editing contents of the execution condition detail setting screen 604 are saved. On the other hand, if a cancel button 613 is clicked by a mouse or the like, the editing contents of the execution condition detail setting screen 604 are discarded, and the detail setting screen 604 is closed.

As in this embodiment, by setting the examination purpose based on the examination request source information, specific processing for the radiographed image can be automatically performed depending on the request source. For example, if radiographing is performed based on the request from the doctor A, the image is automatically copied after radiographing, and monochrome inversion processing can be automatically performed for the copied image.

Third Embodiment

The second embodiment has described the example of efficiently processing the image in accordance with the examination request source information (the favor of the request source doctor) included in the examination information. However, processing according to the favor of the operator can be set. For example, this processing may be a case in which an operator X and an operator Y perform processing using different processing sequences for processing the same image.

Assume that while the operator X manually adjusts image processing when imaging a chest image, the operator Y creates images that have undergone image processing suitable for a lung field, processing for enhancing a catheter tip, and image processing suitable for imaging a mediastinum, and determines an output image. In this case, the operator Y sets the examination purpose corresponding to the processing procedures such that after the first image of the front part of the chest is obtained, the operator Y copies the image three times and applies image processing suitable for the lung field for the first copied image, processing for enhancing the catheter tip for the second copied image, and image processing suitable for the mediastinum for the third copied image.

FIGS. 7A and 7B are views showing an example of a GUI for setting an examination purpose according to the third embodiment. FIG. 7A shows an editing screen, and FIG. 7B shows a detail setting screen for an execution condition. In the editing screen of FIG. 7A, a purpose "front part of chest, operator Y" indicating that the image is for the operator Y and the examination purpose is to radiograph the front part of the chest is input to a purpose input field 701. A character string representing that the protocol is the front part of the chest and the user ID is Y is input to an execution condition setting field 702. This character string can be automatically generated based on the condition set on the execution condition detail setting screen in FIG. 7B.

Settings for performing processing suitable for the lung field, catheter tip highlighting processing, and processing suitable for the mediastinum for three images B, C, and D copied from a radiographed image A are set in image processing blocks 703, 704, and 705, respectively.

In the execution condition detail setting screen shown in FIG. 7B, the operator is selected in an associated item selection field 706 as an associated item in the execution condition detail screen. In this case, the selected item of an additional condition selection field 707 is changed in accordance with the selected item. Two conditions are registered in a condition list display area 708. One is that the protocol name is the "front part of chest", and the second is that the identification information of the operator logged in to the present system is "Operator Y". These two conditions are added. Note that in the execution condition detail setting screen in FIG. 7B, the display of the additional condition selection field 707 is kept empty (blank) because the state is a state immediately after the addition condition selection. "Only for myself" is set in the disclosure range setting field 709. This indicates that the disclosure range of the processing procedure corresponding to the examination purpose set in FIG. 7B can be used by the present operator. Based on the GUI settings in FIGS. 7A and 7B, the condition setting unit 205 can set the identification information of the operator and the disclosure range of the generated processing procedure as the execution conditions of the processing procedure.

As in this embodiment, the specific processing for the radiographed image can be automatically performed by setting the examination purpose and the execution condition based on the information set by the operator. By setting the examination purpose as described above, the above-described image can be automatically obtained when the operator Y who has set the processing procedure performs imaging of the front part of the chest without influencing the operation of another operator at all.

Fourth Embodiment

When an image is copied, a change in numbering condition of the identification information (ID) of an image is required in accordance with the radiogram interpretation order on the PACS side. In the DICOM operation, an image object is expressed in a hierarchical structure of Study, Series, and Image. It is possible to include only one image in one series or include a plurality of images in one series. In this radiographing system, the hierarchical structure of the image can be freely changed in accordance with a DICOM operation. A detail setting unit 206 can perform detail settings of processing (for example, an image copy) set in the editing area of a display unit 104. When copied images of a radiation image are generated as image processing, the detail setting unit 206 can set a hierarchical structure for storing the copied images in accordance with a radiogram interpretation order on the side of the external device such as a PACS.

Figure 8:
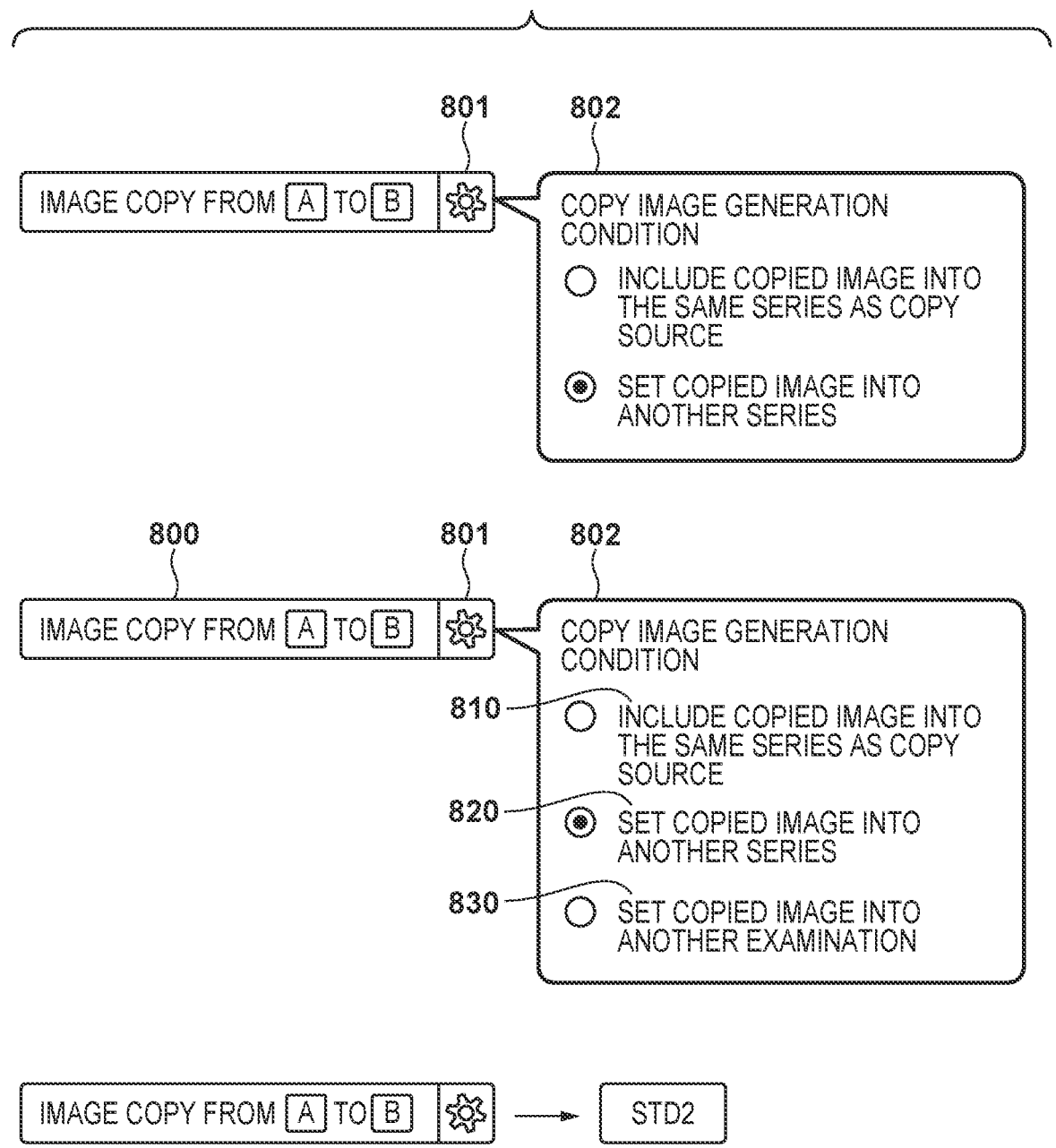
FIG. 8 is a view exemplifying a GUI when setting the details of an image copy block.

FIG. 8 is a view exemplifying a GUI when an image copy block 800 set in a processing editing field 507 in FIG. 5 is to be set in detail. If a detail setting button 801 is clicked, an image copy detail setting screen 802 is displayed by the display control of a display control unit 204. In the image copy detail setting screen 802, the hierarchical structure of the image can be set as the generation condition of the image to be copied.

In FIG. 8, three options, that is, a setting 810 for including a copied image into the same series as that of a copy source, a setting 820 for setting the copied image into another series, and a setting 830 for setting the copied image into another examination can be selected. In the example of FIG. 8, the copied image is set into another series. By selecting one of the options from the image copy detail setting screen 802, the hierarchical structure of the image generated upon copying the radiation image can be freely set. Note that when the operator selects this option, the display control unit 204 can simultaneously perform the display control for closing the image copy detail setting screen 802. According to this embodiment, the processing procedure suitable for the DICOM operation can be set.

Fifth Embodiment

When another examination (another study) is set upon copying an image in the fourth embodiment, a setting 830 for setting the copied image into another examination is selected in an image copy detail setting screen 802 (FIG. 8). In this case, since a new examination is generated, for example, a new examination block corresponding to an examination block 5071 of FIG. 5 is added in a processing editing field 507 of an editing screen 501 shown in FIG. 5.

FIG. 9 is a view showing the display example of an examination block in a processing editing field in the fifth embodiment. If the setting 830 for setting the copied image into another examination is selected in FIG. 8, processing for the copied image is copied as the image of another examination when copying the image radiographed in the first examination. An examination block 901 represents the first examination. An image copy block 902 sets to copy an image A obtained in the first examination as an image B. The generated image B is copied as another examination "STD2". This examination block is set in a state in which the option (setting 830 for setting the copied image into another examination) for setting the copied image into another examination is selected. An examination block 903 indicating the examination "STD2" newly generated upon closing the image copy detail setting screen 802 and an image block 904 showing the image are automatically generated. The monochrome inversion processing is set in the examination block 903 as the specific processing for the image, that is, the processing item (functional block) selected from a functional block display field 505 (FIG. 5).

Referring to FIG. 8, if the setting 830 for setting the copied image into another examination is selected, that is, if a detail setting unit 206 sets that the copied image is generated as the image of the other examination, a selection setting unit 202 sets processing (monochrome inversion processing block in the example of FIG. 9) for the image of the other examination in the processing editing field 507 (editing area) of a display unit 104, and the processing procedure generation unit 203 generates the processing procedure for the image B of the other examination.

According to this embodiment, even if the setting 830 for setting the copied image into another examination is selected as the setting for image copy processing, the processing for the copied image generated from the radiation image obtained in the first examination can be automatically performed by the preset processing procedure by setting the processing procedure for the examination block for another examination.

Sixth Embodiment

In a radiation examination, it may be necessary to change the next processing in accordance with a processing result. For example, if body motion detection processing is performed for a radiographed image, and if it is determined that the body motion is present, re-imaging is performed. This embodiment will describe a setting for a processing procedure in such a case.

Figure 10:
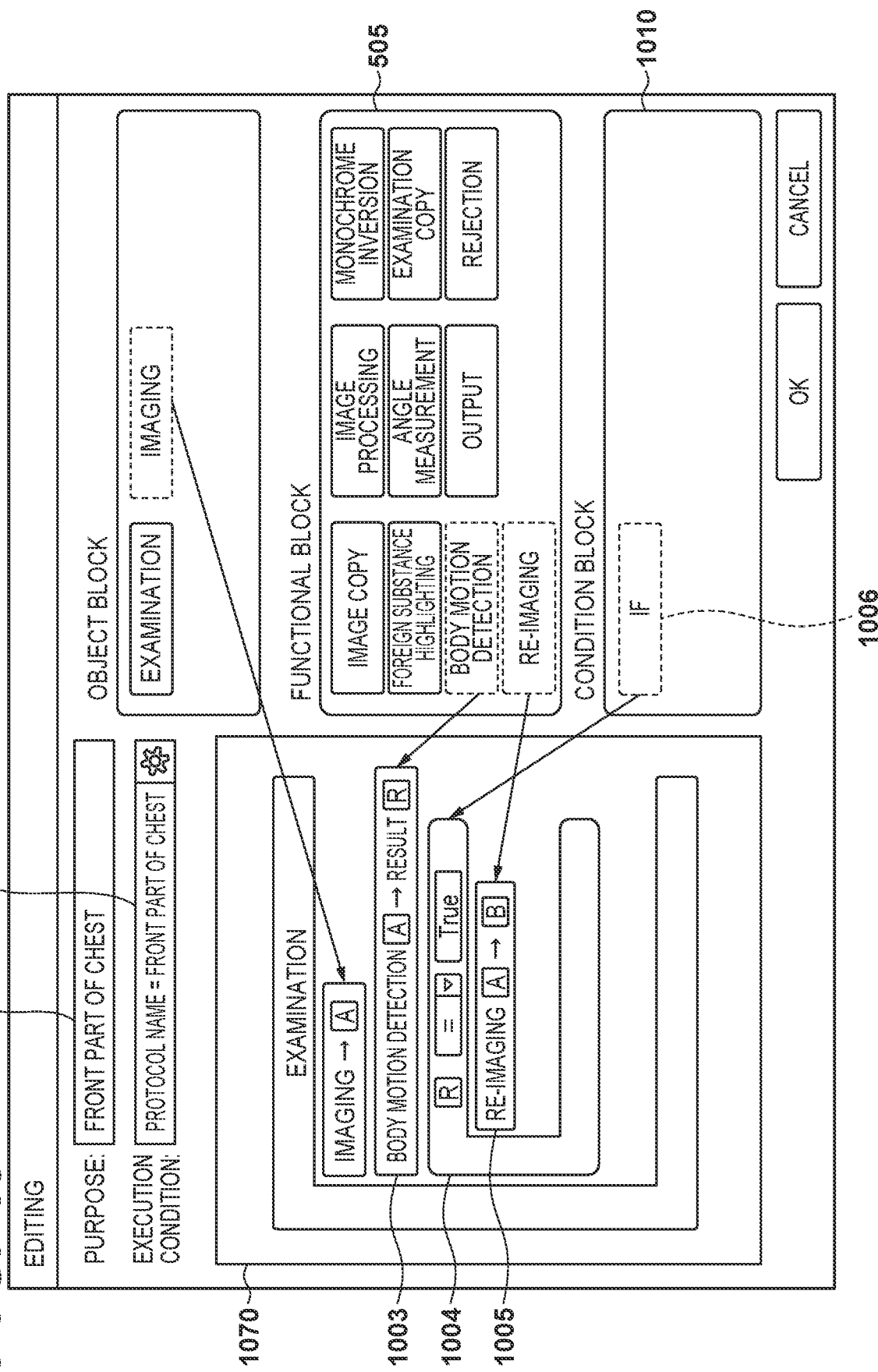
FIG. 10 is a view exemplifying a GUI of a processing procedure including condition determination of body motion detection processing.

FIG. 10 is a view exemplifying a GUI of a processing procedure including a condition determination of the body motion detection processing. The processing procedure is set in which the body motion detection processing is performed for a radiographed image A, and if the determination result is "the body motion is detected (TRUE)", re-imaging is performed. The "front part of chest" is input as the examination purpose in a purpose input field 1001, and execution of the condition when the protocol name is the front part of the chest is set in an execution condition setting field 1002.

If a selection setting unit 202 selects condition determination processing (condition branch processing block) from the display area of a display unit 104, and the selected condition determination processing is set in a processing editing field 507 (editing area) of the display unit 104, a processing procedure generation unit 203 generates the processing procedure for performing the condition determination processing for the processing result.

Referring to FIG. 10, as the specific processing for the radiographed image (image A) from a functional block display field 505, a body motion detection processing block 1003 selected by a drag-and-drop operation using a mouse or the like is set. The body motion detection processing block 1003 performs the body motion detection processing for the image A, and its processing result is stored in a variable R.

A condition branch processing block 1004 can be generated by arranging a condition setting item 1006 in a condition block display field 1010 in an processing editing field 1070 by a drag-and-drop operation, so that the determination condition can be edited.

Assume that a condition "the body motion detection result R is equal to True" is set. This condition can be set by a sign of inequality representing a magnitude relationship in place of a sign of equality. For example, this arrangement can be made such that if a dose index value such as an Exposure Index (EI value) is equal to or less than a given value, re-imaging is performed.

A re-imaging processing block 1005 selected from the functional block display field 505 is set in the processing editing field 1070 in FIG. 10 as the processing procedure with the detected body motion. FIG. 10 shows that the re-imaging processing block 1005 performs re-imaging for the image A and the resultant image is given as B.

According to this embodiment, by setting the processing procedure including the condition determination of the body motion detection processing, the processing for performing re-imaging in accordance with the body motion detection result can be automated.

Seventh Embodiment

If a plurality of examination purposes are defined, execution conditions partially overlap. For example, a case in which the "front part of chest" is set as a protocol name and a case in which the "front part of chest and login operator X" is registered as a protocol name, the execution conditions "front part of chest" overlap as the imaging portions.

According to this embodiment, a condition setting unit 205 can determine the presence/absence of overlapping of execution conditions if a plurality of examination purposes are set. A processing procedure generation unit 203 can generate a processing procedure based on a preset priority if execution conditions overlap. For example, a list display screen of examination purposes displayed in accordance with the priority order in the examination purpose list screen (not shown), the display order can be changed by an operation input of an operation unit 105, thereby causing the processing procedure generation unit 203 to change the priority.

Eighth Embodiment

Assume that a processing procedure is set such that three images are copied after a radiation image is obtained, and image processing is performed for the three copied images. If copy processing is performed immediately after the end of the first radiographing operation and if a deficiency is present in the first image radiographed for the first time, re-imaging is performed after the completion of the copy processing and the image processing.

This embodiment will describe a setting example of a processing procedure for copying a plurality of images from a radiation image obtained as post-processing after imaging is completed and the image is confirmed.

Figure 11:
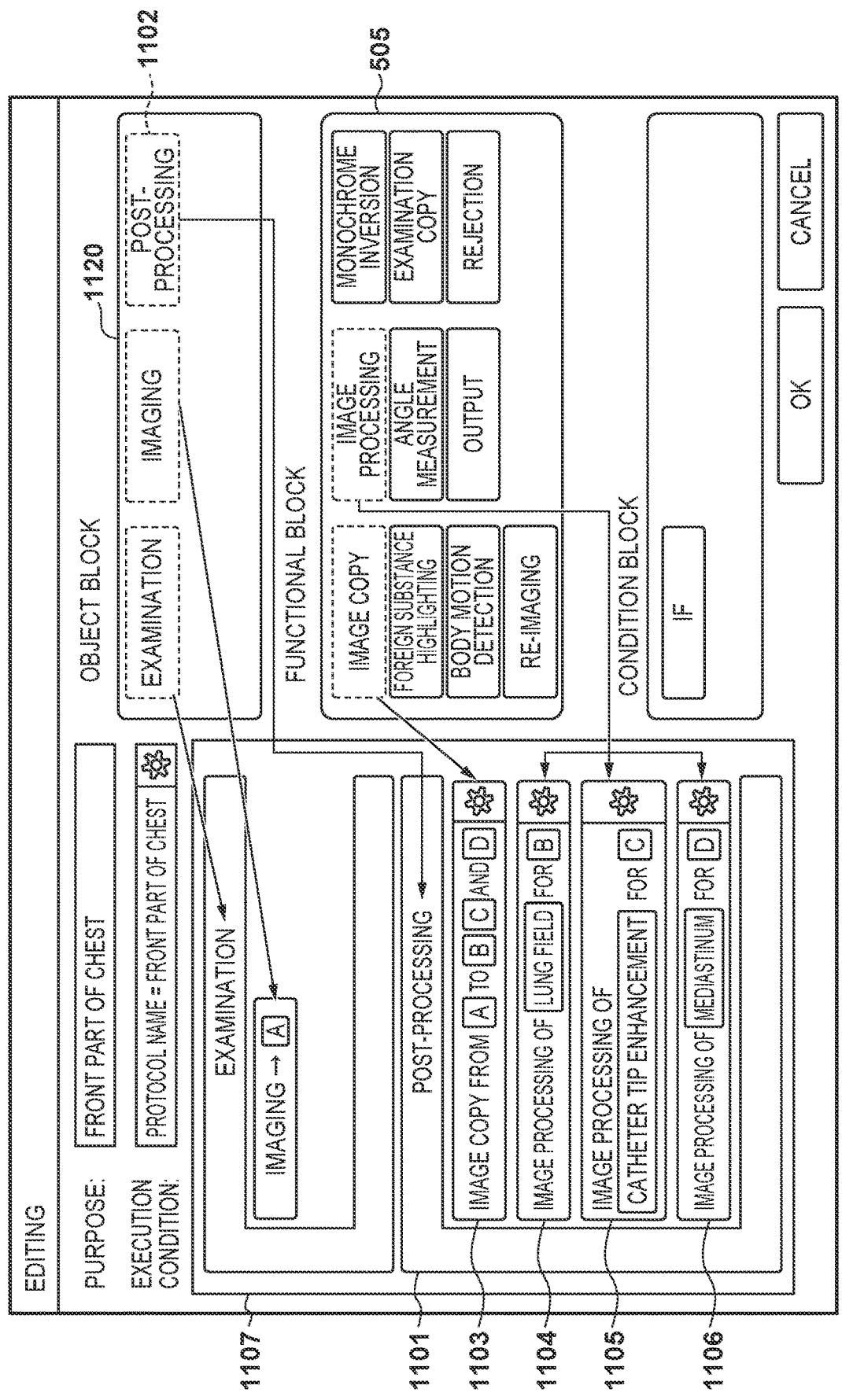
FIG. 11 is a view for explaining a GUI of the radiographing system.

In the GUI in FIG. 11, as a processing procedure, a post-processing block 1101 is set after an image A is obtained in an examination block. The post-processing block 1101 is set after the examination block in a processing editing field 1107 by selecting a post-processing block 1102 of an object block display field 1120 by a drag-and-drop operation using an operation unit 105 such as a mouse.

The post-processing block 1101 is a processing block performed after the completion of all the imaging requested in the examination (all the imaging of the image A in the case of FIG. 11). The post-processing block 1102 of the object block display field 1120 is generated by arranging it into the processing editing field 1107 by a drag-and-drop operation.

In this embodiment, a selection setting unit 202 can select, from the display area of a display unit 104, image processing performed as the post-processing upon the end of imaging of the radiation image and set the image processing in the processing editing field 507 (editing area).

An image copy processing block 1103 indicates that the image A is copied as B, C, and D as post-processing. Image processing blocks 1104 to 1106 indicate that image processing operations are performed for the copied images, respectively. The image copy processing block 1103 and the image processing blocks 1104 to 1106 are generated from a functional block display field 505 as the specific processing items (functional blocks) for the images by a drag-and-drop operation.

FIG. 11 and FIGS. 7A and 7B are different in that processing is performed immediately after the radiation image is obtained in FIGS. 7A and 7B, while various kinds of processing are performed as the post-processing after all the imaging operations in the examination are completed in FIG. 11.

According to this embodiment, the execution timing of the image processing for converting an image obtained by radiography can be arbitrarily set. All the image processing operations are collectively performed as the post-processing upon completion of imaging. This makes it possible to efficiently perform radiography.

Ninth Embodiment

The timing for transferring a radiation image to a PACS changes depending on the contents of an examination in progress. For example, if an unconscious subject is transported, a radiographed image is immediately transferred as an emergency examination. On the other hand, in an outpatient examination, after all the imaging operations for the ordered radiation images end, all the images are transferred.

In this embodiment, an example of setting a processing procedure for an emergency examination as an examination purpose will be described. If a purpose setting unit 201 sets an emergency examination as the purpose of an examination by radiography, a selection setting unit 202 selects an image output from the display area of a display unit 104 as processing of the radiation image corresponding to the emergency examination and sets the image output in an processing editing field 1207 (editing area). A processing procedure generation unit 203 generates the processing procedure corresponding to the purpose of the examination by radiography based on the set processing (imaging of an image A and output of the obtained image).

The emergency examination is input as the examination purpose in a purpose input field 1202 of an editing screen 1201 of FIG. 12. In addition, a case corresponding to the emergency examination is set as an examination type in an execution condition setting field 1203.

An examination block 1271 is set in the processing editing field 1207, and an imaging block 1272 and an image output processing block 1273 are set inside a square U-shaped figure as a series of processing procedures in the examination. The processing procedure generation unit 203 generates a series of processing procedures for processing the radiation image based on a combination of a plurality of set processing operations (the imaging block 1272 and the image output processing block 1273).

In the example of FIG. 12, the "emergency examination" is set as the examination purpose, and a condition in which the examination type is the emergency examination is set as the execution condition. By arranging the output processing block 1273 immediately under the imaging block 1272, the image transfer timing can be set so as to perform the transfer processing after image radiography.

According to this embodiment, by setting the processing procedure corresponding to the emergency examination, when the emergency examination is to be performed, the obtained radiation image can be immediately transferred.

Tenth Embodiment

There exists a case in which after the examination is started upon matching of the examination purpose execution condition, the execution condition is changed midway. For example, even if an order includes the standing position of the front part of the chest, a wheelchair subject may be imaged in a sitting position which is judged by the operator. In this case, the operator presses a cancel button to cancel or change the selected examination purpose.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-072651, filed Apr. 4, 2018, which is hereby incorporated by reference herein in its entirety.

What is claimed is:

1. An information processing apparatus comprising:
at least one memory storing instructions; and
at least one processor that, when executing the instructions, causes the information processing apparatus to function as:
a purpose setting unit configured to set an examination purpose of radiography;
a selection setting unit configured to select, from a display area of a display, processing for an image performed as post-processing upon an end of imaging of a radiation image corresponding to the examination purpose, and set the selected processing for an image in an editing area;
a generation unit configured to generate a processing procedure corresponding to the examination purpose based on the set processing; and
a condition setting unit configured to set an execution condition of the processing procedure based on examination request source information included in examination information received from an external device,
wherein if the selection setting unit selects condition determination processing from the display area of the display and sets the editing area of the display, the generation unit generates the processing procedure for performing the condition determination processing for a processing result,
wherein the purpose setting unit sets the examination purpose based on an input from a GUI displayed on the display or the examination request source information,
wherein the condition setting unit determines presence or absence of overlapping of execution conditions if a plurality of examination purposes are set, and
wherein the generation unit generates the processing procedure based on a preset priority if the execution conditions overlap.

2. The apparatus according to claim 1, wherein the at least one processor, when executing the instructions, further causes the information procession apparatus to function as:
an obtaining unit configured to obtain the examination information from the external device; and an execution unit configured to perform processing of the radiation image based on a processing procedure corresponding to an examination purpose included in the examination information.

3. The apparatus according to claim 1, wherein the selection setting unit selects image processing from an item displayed in the display area of the display as processing of the radiation image and sets the selected image processing in the editing area.

4. The apparatus according to claim 1, wherein if a plurality of pieces of processing of the radiation image are set in the editing area, the generation unit generates a series of processing procedures for performing processing of the radiation image based on a combination of the set plurality of pieces of processing.

5. The apparatus according to claim 3, wherein the at least one processor, when executing the instructions, further causes the information procession apparatus to function as a display control unit configured to change display of processing selectable in the display area of the display in accordance with the examination purpose.

6. The apparatus according to claim 5, wherein the display control unit displays, on the display, a combination of a thumbnail image obtained by reducing an image processed based on the processing procedure and text display indicating contents of the processing procedure.

7. An information processing apparatus comprising:
at least one memory storing instructions; and
at least one processor that, when executing the instructions, causes the information processing apparatus to function as:
a purpose setting unit configured to set an examination purpose of radiography;
a selection setting unit configured to select, from a display area of a display, processing for an image performed as post-processing upon an end of imaging of a radiation image corresponding to the examination purpose, and set the selected processing for an image in an editing area;
a generation unit configured to generate a processing procedure corresponding to the examination purpose based on the set processing; and
a condition setting unit configured to set an execution condition of the processing procedure based on examination request source information included in examination information received from an external device,
wherein if the selection setting unit selects condition determination processing from the display area of the display and sets the editing area of the display, the generation unit generates the processing procedure for performing the condition determination processing for a processing result,
wherein the purpose setting unit sets the examination purpose based on an input from a GUI displayed on the display or the examination request source information, and
wherein the condition setting unit sets identification information of an operator and a disclosure range of the generated processing procedure as the execution condition of the processing procedure.

8. An information processing apparatus comprising:
at least one memory storing instructions; and
at least one processor that, when executing the instructions, causes the information processing apparatus to function as:

a purpose setting unit configured to set an examination purpose of radiography;
a selection setting unit configured to select, from a display area of a display, processing for an image performed as post-processing upon an end of imaging of a radiation image corresponding to the examination purpose, and set the selected processing for an image in an editing area;
a generation unit configured to generate a processing procedure corresponding to the examination purpose based on the set processing; and
a detail setting unit configured to set a hierarchical structure for storing a copied image in accordance with a radiogram interpretation order on an external device side as an image generation condition if the copied image of the radiation image is generated as the image processing,
wherein if the selection setting unit selects condition determination processing from the display area of the display and sets the editing area of the display, the generation unit generates the processing procedure for performing the condition determination processing for a processing result, and
wherein the selection setting unit selects image processing from an item displayed in the display area of the display as processing of the radiation image and sets the selected image processing in the editing area.

9. The apparatus according to claim 8, wherein if the detail setting unit sets that the copied image is generated as an image of another examination, the selection setting unit sets processing for the image of the other examination in the editing area of the display, and the generation unit generates the processing procedure for the image of the other examination.

10. An information processing apparatus comprising:
at least one memory storing instructions; and
at least one processor that, when executing the instructions, causes the information processing apparatus to function as:
a purpose setting unit configured to set an examination purpose of radiography;
a selection setting unit configured to select, from a display area of a display, processing for an image performed as post-processing upon an end of imaging of a radiation image corresponding to the examination purpose, and set the selected processing for an image in an editing area; and
a generation unit configured to generate a processing procedure corresponding to the examination purpose based on the set processing,
wherein if the selection setting unit selects condition determination processing from the display area of the display and sets the editing area of the display, the generation unit generates the processing procedure for performing the condition determination processing for the processing result, and
wherein if the purpose setting unit sets an emergency examination as the examination purpose, the selection setting unit selects an image output from the display area of the display as processing of a radiation image corresponding to the emergency examination, and sets the selected image output in the editing area.

11. An information processing method comprising:
setting an examination purpose of radiography;
selecting, from a display area of a display, processing for an image performed as post-processing upon an end of imaging of a radiation image corresponding to the examination purpose, and set the selected processing for an image in an editing area;

generating a processing procedure corresponding to the examination purpose based on the set processing; and setting an execution condition of the processing procedure based on examination request source information included in examination information received from an external device, wherein if condition determination processing is selected from the display area of the display and the editing area of the display is set, the processing procedure is generated for performing the condition determination processing for the processing result, wherein the examination purpose is set based on an input from a GUI displayed on the display or the examination request source information, wherein in the setting of the execution condition, presence or absence of overlapping of execution conditions is determined if a plurality of examination purposes are set, and wherein in the generating, the processing procedure is generated based on a preset priority if the execution conditions overlap.

12. A non-transitory computer-readable storage medium storing a program for causing a computer to execute each step of the information processing method defined in claim 11.

* * * * *